United States Patent [19]

Schöttle et al.

[11] 4,207,316
[45] Jun. 10, 1980

[54] NOVEL 17-SUBSTITUTED 11 BETA-HYDROXY STEROIDS OF THE PREGNANE SERIES, THEIR MANUFACTURE, PREPARATION AND USE

[75] Inventors: Ernst Schöttle; Alfred Weber; Mario Kennecke; Helmut Dahl; Joachim-Friedrich Kapp; Hans Wendt; Klaus Annen; Henry Laurent; Rudolf Wiechert, all of Berlin, Fed. Rep. of Germany

[73] Assignee: Schering, Aktiengesellschaft, Berlin and Bergkamen, Fed. Rep. of Germany

[21] Appl. No.: 6,693

[22] Filed: Jan. 25, 1979

[30] Foreign Application Priority Data

Jan. 25, 1978 [DE] Fed. Rep. of Germany ....... 2803661
Dec. 19, 1978 [DE] Fed. Rep. of Germany ....... 2855465

[51] Int. Cl.² .......................... C07J 5/00; A61K 31/56
[52] U.S. Cl. ............................... 424/243; 260/397.45; 435/61; 435/911
[58] Field of Search .................... 260/397.45; 424/243

[56] References Cited

U.S. PATENT DOCUMENTS 3,530,038   9/1970   DeFlines et al. ................. 195/51

Primary Examiner—Elbert L. Roberts
Attorney, Agent, or Firm—Millen & White

[57] ABSTRACT

Corticoids of the formula

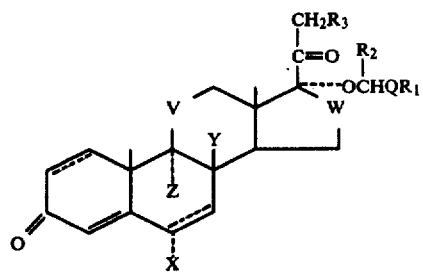

wherein
≂ represents a single bond or a double bond;
X is hydrogen, fluorine, chlorine or methyl;
Y is hydrogen and Z is hydrogen, fluorine or chlorine, or
Y and Z together are a carbon-to-carbon bond;
V is β-hydroxymethylene, β-chloromethylene or carbonyl;
W is methylene, ethylidene or vinylidene;
Q is oxygen or sulfur;
$R_1$ is alkyl of 1–8 carbon atoms, alkyl of 2–8 carbon atoms with an oxygen atom between two of the carbon atoms or benzyl, and $R_2$ is hydrogen or alkyl of 1–4 carbon atoms, or
$R_1$ and $R_2$ collectively are trimethylene or tetramethylene; and
$R_3$ is hydrogen, fluorine, chlorine, hydroxy, or hydroxy esterified by a $C_{1-16}$ hydrocarbon carboxylic acid have valuable pharmacological properties, e.g., anti-inflammatory activity.

79 Claims, No Drawings

NOVEL 17-SUBSTITUTED 11 BETA-HYDROXY STEROIDS OF THE PREGNANE SERIES, THEIR MANUFACTURE, PREPARATION AND USE

CROSS REFERENCE TO RELATED APPLICATIONS

U.S. application Ser. No. 006,692 filed on the same day as this application, and whose disclosure is incorporated by reference herein, concerns related compounds and processes.

BACKGROUND OF THE INVENTION

The present invention concerns novel corticoids, processes for the manufacture thereof, their use and pharmaceutical preparations containing these corticoids.

It has been known for a long time that the topical efficacy of anti-inflammatory 17α-hydroxycorticoids can be increased by esterifying the 17-hydroxy group. (See, in this connection, the summary report by Popper et al, "Anti-inflammatory Steroids in Anti-inflammatory Agents", 1, Academic Press, New York, San Francisco, London [1974]:268–271.)

SUMMARY OF THE INVENTION

It is an object of this invention to further increase the topical efficacy and/or the dissociation between desirable topical anti-inflammatory activity and undesirable systemic effectiveness in the same compounds in a different and more efficient manner.

Upon further study of the specification and appended claims, further objects and advantages of this invention will become apparent to those skilled in the art.

These objects have been achieved by substituting the hydrogen atom of the 17α-hydroxy groups of these corticoids by an acetal residue or a thioacetal residue instead of an ester.

Consequently, this invention especially relates to novel corticoids of Formula I

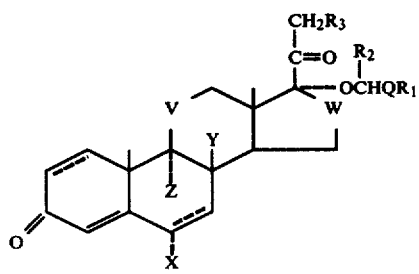

wherein

═ represents a single bond or a double bond;
X is hydrogen, fluorine, chlorine or methyl;
Y is hydrogen and Z is hydrogen, fluorine or chlorine, or
Y and Z together are a carbon-to-carbon bond;
V is β-hydroxymethylene, β-chloromethylene or carbonyl;
W is methylene, ethylidene or vinylidene;
Q is oxygen or sulfur;
$R_1$ is alkyl of 1–8 carbon atoms, alkyl of 2–8 carbon atoms with an oxygen atom between two of the carbon atoms or benzyl, and $R_2$ is hydrogen or alkyl of 1–4 carbon atoms, or $R_1$ and $R_2$ collectively are trimethylene or tetramethylene; and
$R_3$ is hydrogen, fluorine, chlorine, hydroxy, or hydroxy esterified by a $C_{1-16}$ hydrocarbon carboxylic acid.

The invention more particularly relates to corticoids of the formulae Ia-c:

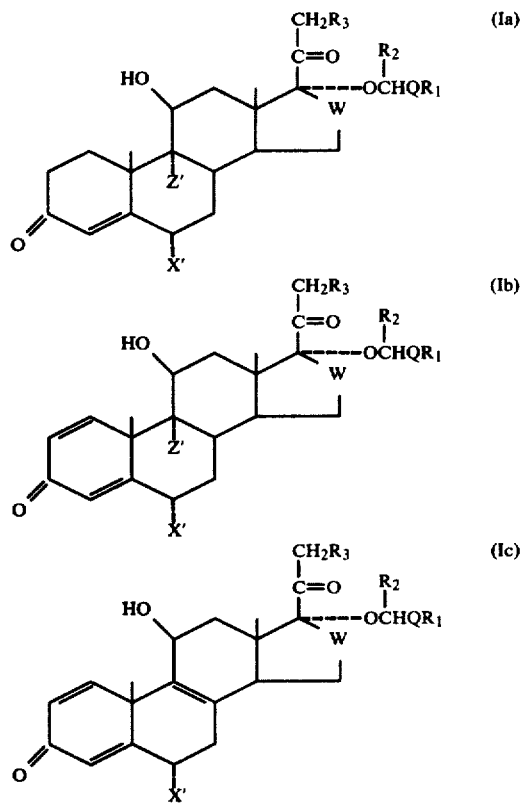

wherein
W, Q, $R_1$, $R_2$ and $R_3$ are as previously defined and
X' is hydrogen, fluorine, or methyl and
Z' is hydrogen, fluorine or chlorine.

DETAILED DISCUSSION

In the novel corticoids of Formula I, $R_1$ can be a straight-chain or branched alkyl residue of 1–8, preferably 1–6 carbon atoms. Suitable alkyl residues include, for example, methyl, ethyl, propyl, isopropyl, butyl, isobutyl, tert-butyl, pentyl, isopentyl, hexyl, heptyl and octyl. $R_1$, can, however, also be a $C_{2-6}$ alkyl group interrupted by a non-terminal oxygen atom. Suitable such residues include, for example, 2-methoxyethoxy, 3-methoxypropoxy and 2-ethoxyethoxy.

In the corticoids of formula I, $R_2$ can be an alkyl group of 1–4 carbon atoms, e.g., methyl, ethyl, propyl, or butyl. Corticoids of formula I wherein $R_2$ is hydrogen are remarkable in that they cannot form diastereomeric mixtures.

The onset of activity and the duration of activity of the novel corticoids, as well as their solubility in physiologically compatible solvents are dependent, just as for conventional corticoids, in particular on whether a hydroxy group in the 21-position is esterified by an acid residue and, sometimes, what the acid is.

Preferred esterified 21-hydroxy groups $R_3$ are acyloxy groups of 1–16 carbon atoms in the acyl residue, generally $C_{1-16}$ hydrocarbon carboxylic acyloxy. Equivalent acyl groups are sulfate groups or phosphate groups. Suitable acyloxy groups include, for example, those derived from straight-chain or branched, saturated or unsaturated aliphatic mono- or dicarboxylic acids; these acids can be substituted in conventional fashion, for example, by hydroxy groups, amino groups, or halogen atoms to form equivalent acyl groups.

Furthermore suitable and equivalent as acyloxy groups are also residues of cycloaliphatic, aromatic, mixed aromatic-aliphatic, or heterocyclic acids, which can likewise be substituted in conventional fashion. Examples of such suitable equivalent acyloxy groups are: formyloxy, acetoxy, propionyloxy, butyryloxy, pentanoyloxy, hexanoyloxy, octanoyloxy, undecanoyloxy, dimethylacetoxy, trimethylacetoxy, diethylacetoxy, tert-butylacetoxy, benzoyloxy, phenacetyloxy, cyclopentylpropionyloxy, hydroxyacetoxy, monochloroacetoxy, dichloroacetoxy and trichloroacetoxy; and furthermore dimethylaminoacetoxy, trimethylaminoacetoxy, diethylaminoacetoxy, piperidinoacetoxy, nicotinoyloxy, ω-carboxypropionyloxy and ω-carboxypentanoyloxy groups.

To produce water-soluble effective agents, the 21-acyloxy compounds with a basic nitrogen group in the acyl residue can be converted into the corresponding acid addition salts, to produce equivalent compounds, e.g., the hydrochlorides, hydrobromides, sulfates, phosphates, oxalates, tartrates or maleates. Furthermore, the 21-dicarboxylic acid monoesters, as well as the sulfuric acid and phosphoric acid esters can be converted into the alkali salts thereof to produce equivalent compounds, for example, the sodium or potassium salts, in order to increase their water solubility.

As is evident from the diverse nature of the illustrative acids named above, the exact structure of the acid residue is not critical. Therefore, contemplated substantial equivalents of the generally preferred hydrocarbon carboxylic acids are those other types of acids named above, e.g., the heterocyclic acids, the substituted acids, the acid addition or alkali salts, etc., as well as other conventional acids whose acyl groups are in vivo hydrolyzable and physiologically acceptable.

Particularly preferred corticoids of formulae Ia-Ic are those wherein X' is H and Z' is H or Z' is F or Cl. Particularly preferred corticoids of formula I are those wherein W is methylene, Q is oxygen, Q is sulfur, $R_2$ is H, $R_2$ is alkyl of 1-6 carbon atoms, $R_3$ is OH or esterified OH and/or $R_3$ is F or Cl.

The novel corticoids of formula I can be prepared, in accordance with the invention, by several processes.

A. For example, the corticoids of formula I can be prepared in a conventional manner from 17α-hydroxy steroids of Formula II

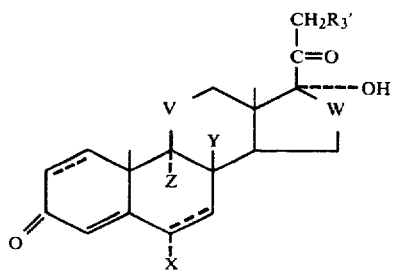
(II)

wherein
$=$, X, Y, Z, V, and W are as defined previously,
$R'_3$ is hydrogen, fluorine, chlorine or an esterified hydroxy group as described above,
optionally after intermediarily protecting an 11β-hydroxy group,
(a) by reaction with an acetal of formula III

(III)

wherein $R_1$ and $R_2$ are as defined for formula I; or
(b) by reaction with an α-halogen ether of formula IV

(IV)

wherein
$R_1$ and $R_2$ are as defined for formula I and
Hal is chlorine, bromine, or iodine; or
(c) by reaction with a vinyl ether of formula V

(V)

wherein
$R_1$ is as defined in formula I and
$R'_2$ is hydrogen or alkyl of 1-3 carbon atoms; or
(d) by reaction with a sulfoxide of formula VI

(VI)

wherein $R_1$ and $R_2$ are as defined for formula I; and
optionally, the corticoids saturated in the 1- and 2-positions obtained in accordance with process variants (a) through (d) may be dehydrogenated in the 1,2-position, and/or an 11β-hydroxy group may be oxidized to an oxo group, and/or a 21-ester group may be saponified and/or a 21-hydroxy group may be esterified or exchanged against fluorine atoms or chlorine atoms.

B. Additionally, for example, the corticoids of formula I may be prepared in a conventional manner, by
(a') chemically adding chlorine or hypochlorous acid to a 9,11-dehydro steroid of formula VII

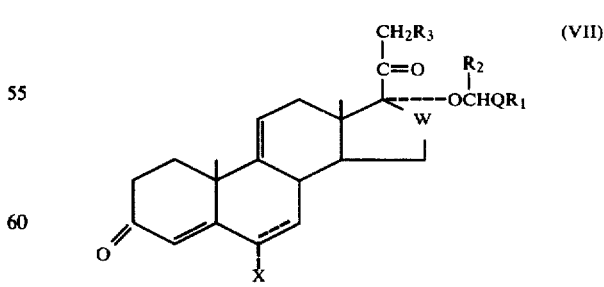
(VII)

wherein $=$, X, W, Q, $R_1$, $R_2$ and $R_3$ are as defined for formula I; or
(b') opening the epoxide ring of a 9,11-epoxy steroid of formula VIII

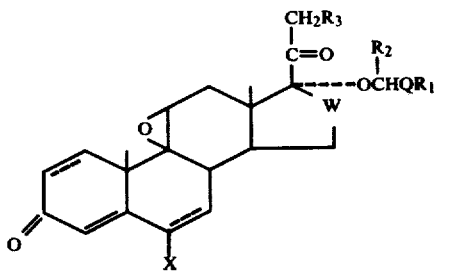

wherein ═, X, W, Q, R₁, R₂ and R₃ are as defined for formula I,
with hydrogen fluoride or hydrogen chloride; or
(c′) splitting off Z″ or HZ″ from a 9-halo steroid of formula IX

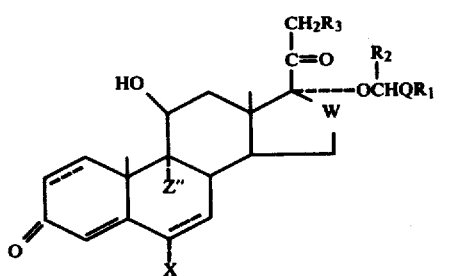

wherein ═, X, W, Q, R₁, R₂ and R₃ are as defined for formula I and
Z″ is chlorine or bromine; and
optionally the corticoids saturated in the 1,2-position obtained according to variants (a′) through (c′) are dehydrogenated in the 1,2-position, and/or an 11β-hydroxy group is oxidized to an oxo group, and/or a 21-ester group is saponified and/or a 21-hydroxy group is esterified or exchanged against fluorine atoms or chlorine atoms.

The compound of formula I can also be prepared by hydroxylating in the 11β- position a compound of the formula

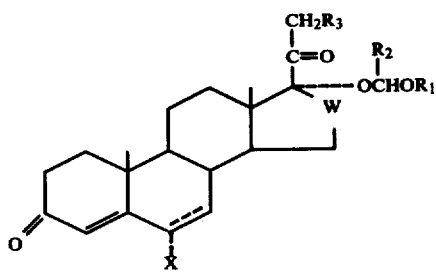

See U.S. application Ser. No. 006,692 filed Jan. 25, 1979, whose disclosure is incorporated by reference herein, for details.

The processes mentioned under A can be conducted under conventional conditions [Synthesis 1975:2786; J. Chem. Soc. 66 (1974):431; J. Amer. Chem. Soc. 74 (1952):1239; U.S. Pat. No. 3,383,394, and "Angew. Chemie" (Applied Chemistry) 90 (1978):289].

Thus, it is possible, for example, to react the steroids of formula II with an acetal of formula III in the presence of an acidic catalyst, e.g., perchloric acid, p-toluenesulfonic acid, or suitably phosphorus pentoxide. This reaction can be carried out in the absence of further solvents or in the presence of inert solvents (chloroform, methylene chloride, tetrachloroethane, tetrachloromethane, toluene, diethyl ether, tetrahydrofuran, dioxane, etc.). The reaction is customarily effected at a reaction temperature of between −20° C. and +50° C. and is particularly suitable for the production of those steroids of formula I wherein R₂ is hydrogen.

Moreover, the steroids of formula II can also be reacted with a vinyl ether of formula V. This reaction is preferably conducted in one of the aforementioned inert solvents with the addition of an acidic catalyst (perchloric acid, p-toluenesulfonic acid, methanesulfonic acid, etc.). The reaction is preferably accomplished at a reaction temperature of −20° C. to 100° C.

Furthermore, the steroids of formula II can also be reacted with an α-halogen ether of formula IV. This reaction can take place, for example, in an inert polar solvent, such as acetonitrile, dimethylformamide, N-methylpyrrolidone or hexamethylphosphoric triamide with the addition of a basic catalyst, e.g., silver oxide, triethylamine or diisopropylethylamine. Preferably, the reaction is conducted at a reaction temperature of −20° C. to +100° C.

During the above-mentioned reactions, the corticoids of formula I wherein Q is oxygen are obtained. To produce corticoids wherein Q is a sulfur atom, the corticoids of formula II can be reacted with sulfoxides of formula VI. This reaction can be effected, for example, by reacting the sulfoxide and the steroid, optionally in an inert solvent (methylene chloride, tetrachloroethane, tetrahydrofuran, etc.), with the addition of an anhydride (preferably acetic anhydride) and an acidic catalyst (acetic acid, boron trifluoride, etc.), at about −20° C. to 100° C.

When using, as the starting compounds for the processes of this invention listed under A, the 11β-hydroxycorticoids of formula II, it is advantageous to intermediarily protect the 11β-hydroxy group to avoid its partial acetalization. This can be done, for example, by converting the 11β-hydroxy group prior to acetalization into the corresponding nitrate, formate, or trihaloacetate (especially trifluoroacetate) and then cleaving these esters after conducting the process in accordance with reactions A(a)–A(d).

The esterification of the 11β-hydroxycorticoids with nitric acid can be effected, for example, with acetyl nitrate, prepared by mixing fuming nitric acid with acetic anhydride. After the acetalization has been accomplished, the nitrates can then be converted back into the 11β-hydroxycorticoids by reaction with zinc dust in acetic acid.

The esterification of the 11β-hydroxycorticoids with formic acid can be effected, for example, by means of formic acid-acetic anhydride with the use of 4-dimethylaminopyridine as the catalyst. After the 17α-acetalization has been accomplished, the thus-obtained 11β-formyloxycorticoids can then be converted into the corresponding 11β-hydroxy steroids by the use of alkaline hydrolysis (e.g., by means of sodium methylate solution) or by enzymatic saponification.

The esterification of the 11β-hydroxycorticoids with trihaloacetic acid—especially trifluoroacetic acid—can be conducted, for example, by reacting the 11β-hydroxycorticoids with trihaloacetic anhydride in pyridine. After the 17α-acetalization has been effected, the trihaloacyl group can then be split off again by hydrolysis (for example in a lower alcohol with the addition of a weakly alkaline catalyst, e.g., sodium acetate or triethylamine).

The processes listed under B can likewise be conducted under conditions known per se (U.S. Pat. Nos. 3,678,034; 3,718,671; 3,845,085; and 3,894,063).

Thus, the 9,11-dehydro steroids of formula VII can be reacted in an inert solvent (acetic acid, tetrahydrofuran, dioxane, acetonitrile, etc.), for example, with reagents which release hypochlorous acid during the course of the reaction in the presence of water and an acid (sulfuric acid, phosphoric acid, perchloric acid, etc.), i.e., reagents which form halogen cations, e.g., N-chloroacylamides (especially N-chloroacetamide) or N-chloroacylimides (particularly N-chlorosuccinimide). In this reaction, the 9α-chloro-11β-hydroxycorticoids of formula I are obtained as the primary products; frequently, the corresponding 9α,11β-dichlorocorticoids of formula I are obtained as by-products. The latter are obtained as the main products if the reaction is conducted under the exclusion of water in the presence of hydrogen chloride as the acid.

On the other hand, the epoxy ring of 9,11-epoxy steroids of formula VIII can be opened with hydrogen chloride or hydrogen fluoride, for example, by dissolving the compounds of formula IV in an inert solvent saturated with hydrogen chloride or hydrogen fluoride and optionally additionally introducing gaseous hydrogen chloride into this solution. Suitable inert solvents are, for example, ethers (diethyl ether, diisopropyl ether, dioxane, tetrahydrofuran, etc.) or chlorinated hydrocarbons (methylene chloride, chloroform, carbon tetrachloride, tetrachloroethane, etc.). During this reaction, the 9α-fluoro- and/or 9α-chloro-11β-hydroxycorticoids of formula I are produced.

To split off halogen from the 9-halo steroids of formula IX, these compounds can be reacted, for example, in an inert solvent in the presence of radical-forming agents (azobisisobutyronitrile, di-tert-butyl peroxide, UV light, etc.) with trialkyl tin hydrides (triethyltin hydride, tributyltin hydride, etc.). Suitable inert solvents are, for instance, ethers (diethyl ether, glycol dimethyl ether, dioxane, tetrahydrofuran), hydrocarbons (cyclohexane, benzene, toluene, etc.), alcohols (methanol, ethanol, isopropanol, etc.), or nitriles (acetonitrile, etc.). During this reaction, the 9α-unsubstituted 11β-hydroxycorticoids of formula I are produced.

The splitting off of hydrogen halide from the 9-halo steroids of formula IX takes place under the conditions customarily employed in steroid chemistry for splitting off hydrogen halide from halohydrins.

The compounds of formula IX can thus be heated, for example, under reflux in a tertiary amine, such as pyridine, lutidine, or especially collidine. Another suitable method for splitting off hydrogen bromide, is, for example, the reaction of these compounds with lithium salts (lithium chloride, etc.) and/or calcium carbonate in dimethylformamide or dimethylacetamide. In these reactions, the Δ⁸-corticoids of formula I are produced.

The starting compounds of formulae VII through IX required for the processes of this invention listed under B, can be prepared by acetalizing the corresponding 17α-hydroxy steroids under the conditions of the reactions listed under A; or from the corresponding 17-acetalized corticoids unsubstituted in the 9-position, by dehydrating the same to the 9,11-dehydro steroids of formula VII, chemically adding HBr to the 9,11-double bond, and converting the thus-obtained 9-bromo steroids of formula IX with bases into the epoxides of formula VIII. The compounds of formula II are fully conventional. Some can also be prepared by the process E below.

The products obtained in accordance with the processes listed under A(a-d) and B(a'-c') can be further converted, if desired, by dehydrogenating the 1,2-saturated corticoids in the 1,2-position, and/or by oxidizing an 11β-hydroxy group of these compounds to an 11-oxo group, and/or by saponifying any 21-ester groups and/or by esterifying any 21-hydroxy groups or exchanging the same against fluorine atoms or chlorine atoms.

The conditions under which the corticoids saturated in the 1,2-position are dehydrogenated in the 1,2-position will be described hereinbelow. All of these optional steps are fully conventional unless otherwise specified herein.

A preferred method resides in esterifying the 21-hydroxy group with a sulfonic acid, preferably with methanesulfonic acid or p-toluenesulfonic acid and then exchanging the sulfonic acid group against halogen. The esterification of the 21-hydroxy group takes place, for example, by treating the 21-hydroxy steroids with a sulfonic acid chloride in the presence of an organic base, such as pyridine, or in the presence of an aqueous alkali. The exchange of the sulfonic acid group against a halogen atom is preferably effected by reacting the 21-sulfonic acid esters with an alkali halogenide, e.g., lithium chloride or potassium hydrogen fluoride in the presence of a polar solvent, such as, for example, dimethylformamide, at a reaction temperature of 50°–180° C.

Other aspects of this invention are processes for the preparation of 11β-hydroxy steroids of the pregnane series having an acetal residue in the 17α-position represented by Formula X

(X)

and/or of certain 11β-hydroxycorticoids of formula I, i.e., of formula I(d) below, and the use of the latter as intermediates for the production of certain steroids of formula XII as mentioned below. These reactions are summarized as follows:

C. A process for preparing an 11β-hydroxy steroid of the pregnane series or a 21-ester thereof, substituted in the 17α-position by an acetal residue of Formula X

(X)

wherein $R_1$ is alkyl of 1–8 carbon atoms, alkyl of 2–8 carbon atoms with an oxygen atom between two of the carbon atoms, or benzyl, and $R_2$ is hydrogen or alkyl of 1–4 carbon atoms, or $R_1$ and $R_2$ collectively are trimethylene or tetramethylene;

comprises fermenting the corresponding 11-deoxy steroid using a fungal culture of the genus Curvularia.

D. A process for preparing an 11β-hydroxy steroid of formula I having the Formula Id

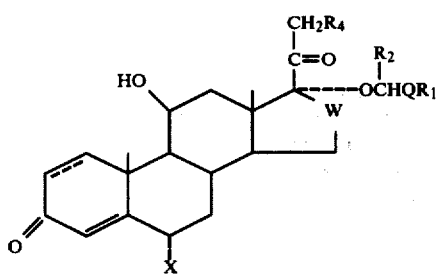

wherein

=X, W, Q, $R_1$ and $R_2$ are as defined for formula I and $R_4$ is hydrogen or hydroxy, comprises fermenting an 11-deoxy steroid of the Formula XI

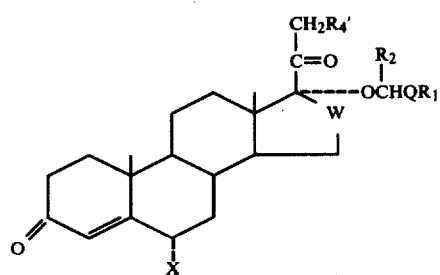

wherein $R_4'$ is hydrogen, hydroxy or alkanoyloxy of 1-6 carbon atoms, with a fungal culture of the genus Curvularia; and optionally dehydrogenating the 1,2-position of the thus-obtained compound of formula Id wherein == is a single bond.

The processes C and C are preferably conducted using a fungal culture of the species Curvularia lunata.

E. A process for preparing a steroid of the Formula XII

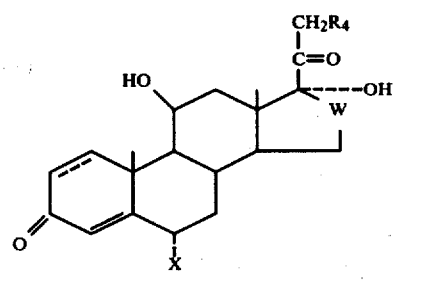

wherein == X, W, and $R_4$ are as defined for formula Id, comprises deacetalizing a compound of the formula

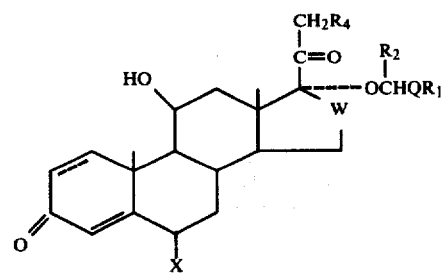

Wherein $R_1$ and $R_2$ are also as defined for formula Id, by treating it under acidic conditions effective to cleave the acetyl group.

As is known, 11β-hydroxy steroids having anti-inflammatory activity (such as, for example, the corticoids: hydrocortisone, prednisolone, dexamethasone, betamethasone, prednylidene, triamcinolone, fluocinolone, or flurandrenolone) are prepared by means of very expensive, multistage partial syntheses from naturally occurring steroids (such as diosgenin), the procuring of which in adequate amounts is meeting with increased difficulty. Within the multistage syntheses of these compounds, the microbiological introduction of the 11β-hydroxy group into the steroid skeleton normally is the most costly and most wasteful step of any synthesis.

A process was developed in 1966, whereby the yield of the 11β-hydroxylation of 11-deoxy-17α-hydroxy steroids of the pregnane series could be substantially increased by esterifying the 17α-hydroxy group, then conducting a hydroxylation using fungi of the genus Curvularia, and saponifying the thus-obtained 11β-hydroxy-17α-acyloxy steroids German Pat. No. 1,618,599=U.S. Pat. No. 3,530,038, whose disclosures are incorporated by reference herein for details of the process). However, the acylation of the 17-hydroxy group is rather expensive; and the yields obtained thereby are frequently unsatisfactory.

The hydrolysis of the 11β-hydroxy-17α-acyloxy steroids is likewise difficult, since by-products are frequently formed, thus requiring an expensive and wasteful purification of the thus-obtained products in order to satisfy the purity criteria demanded of active medicinal agents.

In contrast thereto, the processes C-E of this invention are superior in that the starting steroids can be prepared in good yields from the corresponding 17-hydroxy steroids. Moreover, the products of the process of this invention can be hydrolyzed rapidly and quantitatively to the corresponding 11β,17α-dihydroxy steroids. Thus, two of the major disadvantages of the prior art processes are eliminated.

The starting steroids employed in the process of this invention can also be substituted in the usual way and/or can contain double bonds.

The presence of hydroxy groups or acyloxy groups, for example, in the 21-position, and the presence of halogen atoms, e.g., fluorine, methyl groups, or methylene groups, e.g., in the 6- and/or 16-positions, does not affect the operability of the process of this invention. For purposes of the process of this invention, the starting material steroids preferably possess an oxo group in the 3-position and a double bond in the 4,5-position.

Apart from the use of different starting compounds, the process of this invention is conducted under the conditions customarily employed for the 11β-hydroxylation of steroids using fungi of the genus Curvularia.

Specific fungi of the genus Curvularia suitable for hydroxylation include, for example, Curvularia falcuta QM-102 H, Curvularia genticulata IFO (6284), Curvularia lunata NRRL 2380, NRRL 2434, ATCC 12017 or IFO (6286) and Curvularia maculans IFO (6292).

It is also to be noted that other 11β-hydroxylating microorganisms besides those of the genus Curvularia can be used for conducting the process of this invention, thereby forming equivalent processes; however, normally, this does not afford any advantages in comparison to the preferred process of this invention.

Under the culturing conditions normally employed for these microorganisms, submerged cultures are grown in a suitable nutrient medium under aeration. Then the substrate (dissolved in a suitable solvent or preferably in emulsified form) is added to the cultures, and the latter are fermented until maximum substrate conversion has been attained.

Suitable substrate solvents include, for example, methanol, ethanol, glycol monomethyl ether, dimethylformamide or dimethyl sulfoxide. The substrate can be emulsified, for example, by introducing it through nozzles under strong turbulence into water (preferably decalcified) containing conventional emulsifying aids; the substrate being in micronized form or dissolved in a water-miscible solvent (such as methanol, ethanol, acetone, glycol monomethyl ether, dimethylformamide or dimethyl sulfoxide). Suitable emulsifiers include nonionic emulsifiers, e.g., ethylene oxide adducts or fatty acid esters or polyglycols. Examples of suitable emulsifiers are the commercially available surfactants "Tegin", "Tagat", "Tween" and "Span".

The emulsification of the substrate frequently makes it possible to attain increased substrate throughput and thus an increase in the substrate concentration. However, it is, of course, also possible to employ in the process of this invention other methods for raising the substrate throughput. These are well-known to those skilled in the art of fermentation.

The optimum substrate concentration, time of substrate addition and duration of fermentation are dependent on the structure of the substrate employed and on the type of microorganism utilized. These variables must be determined, as generally necessary in microbiological steroid conversions, in each individual case by preliminary experiments well-known to those skilled in the art.

The dehydrogenation of the $\Delta^4$-steroids saturated in the 1-position per formula I, following as an optional measure, can be effected by means of microbiological working methods as well as by means of purely chemical methods. Thus, it is possible, for example, to dehydrogenate the $\Delta^4$-steroids in the 1-position under the usual conditions with bacterial cultures of the genus Bacillus (e.g., *Bacillus lentus* or *Bacillus sphaericus*) or Arthrobacter (e.g., *Arthrobacter simplex*). On the other hand, however, it is also possible to conduct the $\Delta^1$-dehydrogenation by heating the $\Delta^4$-steroids in inert solvents with the oxidizing agents customary for this reaction, such as, for example, selenium dioxide or 2,3-dichloro-5,6-dicyanobenzoquinone.

The thus-obtained products of the process can be split by simple methods to the corresponding $11\beta,17\alpha,21$-trihydroxy steroids.

This splitting step is conducted under conditions conventionally employed for hydrolysis or alcoholysis of acetals. The compounds can thus be split, for example, by reacting them (in a lower alcohol, such as methanol or ethanol; or in an aqueous organic solvent, such as glycol monomethyl ether, tetrahydrofuran, dioxane, dimethylformamide, dimethyl sulfoxide, hexamethylphosphoric triamide or acetone) with a mineral acid, e.g., hydrochloric acid, sulfuric acid, phosphoric acid, perchloric acid; a sulfonic acid, such as p-toluenesulfonic acid; a strongly acidic carboxylic acid, e.g., formic acid, acetic acid, trifluoroacetic acid; an acidic ion exchanger; or with a Lewis acid, such as boron trifluoride, zinc chloride, zinc bromide or titanium tetrachloride.

The novel corticoids of formula I are distinguished, as mentioned above, upon topical administration by a very high anti-inflammatory activity in mammals, including humans, and, moreover, possess a very favorable dissociation between the desired topical efficacy and any undesired systemic side effects.

The topical efficacy can be determined as follows using the vasoconstriction test.

The test was conducted on respectively eight healthy test persons of both sexes, who had not received any local corti costeroid treatment within the preceding two weeks. After the stratum corneum on the test persons' backs was removed down to the stratum lucidum (20–40 times application and tearing off of an adhesive film), respectively 0.1 g. of the preparations was applied to areas of a size of 4 cm$^2$ without protective dressing. To avoid the application of the identical preparation to identical skin areas, the application is done in a rotating fashion. The vasoconstriction is evaluated visually after 4 and 8 hours by the investigator in accordance with the following grades of effectiveness: 1 = absolute fading; 2 = minor residual erythema; 3 = medium-grade erythema, reddening intensity in the central zone of stripped, untreated and undamaged skin; 4 = erythema with minor fading; 5 = no fading, or intensification of erythema.

The individual evaluations were averaged.

In each test series, diflucortolone 21-valerate ($=6\alpha,$-9$\alpha$-difluoro-11$\beta$-hydroxy-16$\alpha$-methyl-21-valeryloxy-1,4-pregnadiene-3,20-dione=DFV) is utilized as the reference compound.

The difference $\Delta$ of the average degrees of efficacy of DFV and of the test compound determined in the individual series of investigations is calculated in each case. Positive deviations $\Delta$ show a more favorable evaluation: negative deviations show a more unfavorable evaluation of the test compound as compared to DFV.

The tables set forth below list the observed test results obtained when treating the test persons with a preparation containing 0.1 p.p.m. of active agent.

The systemic effectiveness of the compounds can be determined with the aid of the adjuvant edema test as follows:

SPF rats weighing 130–150 g. are injected in the right hind paw, for producing a center of inflammation, with 0.1 ml. of a 0.5% *Mycobacterium butyricum* suspension (obtainable from the U.S. company Difco). Prior to injection, the paw volume of the rats is measured. Twenty-four hours after injection, the paw volume is measured once again to determine the extent of the edema. Thereafter, varying amounts of the test compound—dissolved in a mixture of 29% benzyl benzoate and 71% castor oil—are administered orally or subcutaneously to the rats. After another 24 hours, the paw volume is again determined.

The control animals are treated in the same way, except that they are injected with a benzyl benzoate-castor oil mixture free of test compound.

From the paw volumes determined, the amount of test compound required for attaining a 50% reduction in volume of the experimentally produced paw edema is calculated in the usual way.

The following tables indicate the thus-obtained test results, wherein in each case the compounds of this invention are compared with the conventional corticoids contained in commercially available preparations which are most analogous in structure.

TABLE 1

Test Results of Hydrocortisone Derivatives

| No. | Compound | Vasoconstriction Test ΔAfter 4 h. | Vasoconstriction Test ΔAfter 8 h. | Adjuvant Edema Test (mg./kg. Animal) $ED_{50}$ p.o. | Adjuvant Edema Test (mg./kg. Animal) $ED_{50}$ s.c. |
|---|---|---|---|---|---|
| 1 | 17α-Butyryloxy-11β,21-dihydroxy-4-pregnene-3,20-dione (= hydrocortisone 17-butyrate) | −0.2 | −0.3 | 54 | 13 |
| 2 | 11β,21-Dihydroxy-17α-methoxy-methoxy-4-pregnene-3,20-dione | +0.3 | +0.7 | 67 | 13 |
| 3 | 17α-Ethoxymethoxy-11β,21-dihydroxy-4-pregnene-3,20-dione | 0.0 | +0.7 | | 14.5 |
| 4 | 11β,21-Dihydroxy-17α-propoxy-methoxy-4-pregnene-3,20-dione | +0.4 | +0.4 | | about 10 |
| 5 | 11β,21-Dihydroxy-17α-isopropoxy-methoxy-4-pregnene-3,20-dione | +0.9 | +0.5 | | >30 (42%) |
| 6 | 17α-Butoxymethoxy-11β,21-dihydroxy-4-pregnene-3,20-dione | +0.9 | +0.6 | | 20 |
| 7 | 11β,21-Dihydroxy-17α-(2'-tetrahydropyranyloxy)-4-pregnene-3,20-dione | +0.8 | +0.6 | | 12 |

TABLE 2

Test Results of Prednisolone Derivatives

| No. | Compound | Vasoconstriction Test ΔAfter 4 h. | Vasoconstriction Test ΔAfter 8 h. | Adjuvant Edema Test (mg./kg. Animal) $Ed_{50}$ p.o. | Adjuvant Edema Test (mg./kg. Animal) $ED_{50}$ s.c. |
|---|---|---|---|---|---|
| 8 | 11β,17α,21-Trihydroxy-1,4-pregnadiene-3,20-dione (= prednisolone) | −0.9 | −0.8 | 8.6 | 2.6 |
| 9 | 11β,21-Dihydroxy-17α-methoxy-methoxy-1,4-pregnadiene-3,20-dione | −0.2 | −0.3 | 9.8 | |
| 10 | 21-Acetoxy-11β-hydroxy-17α-methoxymethoxy-1,4-pregnadiene-3,20-dione | +0.7 | +0.4 | | >3 (25%) |
| 11 | 21-Acetoxy-11β-hydroxy-17α-methylthiomethoxy-1,4-pregnadiene-3,20-dione | +0.4 | +0.4 | | about 3 |
| 12 | 21-Butyryloxy-11β-hydroxy-17α-methoxymethoxy-1,4-pregnadiene-3,20-dione | +0.2 | +0.2 | | about 3 |

TABLE 3

Test Results of 9-Chlorocorticoids

| No. | Compound | Vasoconstriction Test ΔAfter 4 h. | Vasoconstriction Test ΔAfter 8 h. | Adjuvant Edema Test (mg./kg. Animal) $ED_{50}$ p.o. | Adjuvant Edema Test (mg./kg. Animal) $ED_{50}$ s.c. |
|---|---|---|---|---|---|
| 13 | 9α-Chloro-11β-hydroxy-16β-methyl-17α,21-dipropionyloxy-1,4-pregnadiene-3,20-dione (= beclomethasone dipropionate) | −0.3 | 0.0 | 22 | 3.0 |
| 14 | 21-Acetoxy-9α-chloro-11β-hydroxy-17α-methoxymethoxy-4-pregnene-3,20-dione | +0.4 | +0.7 | | 3.2 |
| 15 | 21-Acetoxy-9α-chloro-11β-hydroxy-17α-methoxymethoxy-1,4-pregnadiene-3,20-dione | +0.9 | +1.0 | | about 1 |
| 16 | 21-Acetoxy-9α-chloro-11β-hydroxy-17α-(2'-methoxyethoxymethoxy)-1,4-pregnadiene-3,20-dione | +1.0 | +1.3 | about 8 | |

TABLE 4

Test Results of 9-Fluorocorticoids

| No. | Compound | Vasoconstriction Test ΔAfter 4 h. | Vasoconstriction Test ΔAfter 8 h. | Adjuvant Edema Test (mg./kg. Animal) $ED_{50}$ p.o. | Adjuvant Edema Test (mg./kg. Animal) $ED_{50}$ s.c. |
|---|---|---|---|---|---|
| 17 | 9α-Fluoro-11β-hydroxy-16β-methyl-17α,21-dipropionyloxy-1,4-pregnadiene-3,20-dione (= betamethasone dipropionate) | −0.5 | −0.7 | | 2.1 |

TABLE 4-continued

Test Results of 9-Fluorocorticoids

| No. | Compound | Vasoconstriction Test | | Adjuvant Edema Test (mg./kg. Animal) | |
|---|---|---|---|---|---|
| | | ΔAfter 4 h. | ΔAfter 8 h. | ED$_{50}$ p.o. | ED$_{50}$ s.c. |
| 18 | 21-Chloro-9α-fluoro-11β-hydroxy-16β-methyl-17α-propionyloxy-1,4-pregnadiene-3,20-dione (= clobetasol propionate) | +0.5 | +1.1 | | 0.13 |
| 19 | 21-Chloro-9α-fluoro-11β-hydroxy-17α-methoxymethoxy-1,4-pregnadiene-3,20-dione | +0.5 | +0.5 | | 1.9 |
| 20 | 21-Acetoxy-9α-fluoro-11β-hydroxy-17α-methoxymethoxy-4-pregnene-3,20-dione | +0.6 | +0.5 | | 2.0 |
| 21 | 9α-Fluoro-11β-hydroxy-17α-methoxymethoxy-21-propionyloxy-1,4-pregnadiene-3,20-dione | +0.2 | +0.7 | | 3.0 |
| 22 | 9α-Fluoro-11β-hydroxy-17α-methoxymethoxy-16β-methyl-21-propionyloxy-1,4-pregnadiene-3,20-dione | +0.5 | +1.0 | | 3.0 |
| 23 | 21-Acetoxy-9α-fluoro-11β-hydroxy-16β-methyl-17α-methylthiomethoxy-1,4-pregnadiene-3,20-dione | +0.5 | +0.2 | | about 1 |

TABLE 5

Test Results of 6-Fluoro- and 6-Methylcorticoids

| No. | Compound | Vasoconstriction Test | | Adjuvant Edema Test (mg./kg. Animal) | |
|---|---|---|---|---|---|
| | | ΔAfter 4 h. | ΔAfter 8 h. | ED$_{50}$ p.o. | ED$_{50}$ s.c. |
| 24 | 6α-Fluoro-11β,21-dihydroxy-16α-methyl-1,4-pregnadiene-3,20-dione | −1.1 | −0.8 | | 3.5 |
| 25 | 6α-Fluoro-11β,21-dihydroxy-17α-methoxymethoxy-4-pregnene-3,20-dione | +0.1 | +0.1 | | 4.0 |
| 26 | 11β,17α,21-Trihydroxy-6α-methyl-1,4-pregnadiene-3,20-dione (= 6-methylprednisolone) | −0.8 | −0.9 | | |
| 27 | 11β,21-Dihydroxy-17α-(1'-methoxyethoxy)-6α-methyl-4-pregnene-3,20-dione | +0.6 | +0.6 | 22 | |

The novel compounds are suitable in combination with the vehicles customary in galenic pharmacy for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin diseases.

The drug specialities are prepared in the usual way by converting the active agents with suitable additives into the desired form of administration, such as, for example: solutions, lotions, ointments, creams, or plasters. In the thus-formulated medicines, the concentration of active ingredient is dependent on the form of application. In case of lotions and ointments, an active agent concentration of 0.001% to 1% is preferably used.

Moreover, the novel compounds, optionally in combination with the customary vehicles and auxiliary agents, are also well suitable for the manufacture of inhalants usable for therapy in allergic diseases of the respiratory tract, as for example bronchial asthma or rhinitis.

The novel corticoids are also usable for the treatment of allergic diseases of the intestinal tract, such as colitis ulcerosa and colitis granulomatosa, also in the form of capsules, tablets, or dragees containing preferably 10–200 mg. of active agent and being applied orally, or in the form of suspensions containing preferably 100–500 mg. of active agent per dosage unit and which are applied rectally.

The administration of the compounds as inhalants or to treat the intestinal tract is fully conventional, e.g., analogous to beclomethasone 17,21-dipropionate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(a) 21.63 g. of 3β,21-diacetoxy-17α-hydroxy-5-pregnen-20-one is dissolved in 150 ml. of anhydrous methylene chloride and 100 ml. of anhydrous formaldehyde dimethylacetal. The solution is then cooled with water and introduced into a mixture of 21.6 g. of phosphorus pentoxide and 43 g. of kieselguhr, and the mixture is stirred for one hour at room temperature. The reaction mixture is then filtered, the residue is washed with methylene chloride, triethylamine is added to the filtrate until a pH of 9 has been reached, and the mixture is concentrated under vacuum. The residue is recrystallized from methanol/methylene chloride, thus obtaining 22.68 g. of 3β,21-diacetoxy-17α-methoxymethoxy-5-pregnen-20-one, m.p. 182°-184° C.

(b) A 2-liter Erlenmeyer flask containing 1 liter of sterile nutrient solution which contains 0.3% yeast extract, 0.3% corn steep liquor, and 0.2% glucose—adjusted to pH 7.0—is inoculated with a dry culture of *Flavobacterium dehydrogenans* ATCC 13 930 and shaken at 30° C. for two days at 175 r.p.m.

A 500-milliliter Erlenmeyer flask with 85 ml. of the same nutrient medium is inoculated with 10 ml. of the *Flavobacterium dehydrogenans* germination culture and shaken at 175 r.p.m. at 30° C. for 7 hours. Then 5 ml. of a sterile solution of 0.5 g. of 3β,21-diacetoxy-17α-methoxymethoxy-5-pregnen-20-one in dimethylformamide is added to the culture, and the latter is shaken at 30° C. for another 65 hours at 175 r.p.m. After fermentation has been completed, the culture is extracted twice with 100 ml. of ethylene chloride. The extract is concentrated under vacuum, the residue is purified by chromatograpy over aluminum oxide, and the yield is 402 mg. of 21-hydroxy-17α-methoxymethoxy-4-pregnene-3,20-dione, m.p. 152°-153° C.

(c) A 2-liter Erlenmeyer flask with 1 liter of a sterile nutrient solution containing 2% glucose and 2% corn steep liquor—adjusted to pH 6.5—is inoculated with a supernatant broth of a dry culture of *Curvularia lunata* NRRL 2380 and shaken at 175 r.p.m. for 60 hours at 30° C.

A 500-milliliter Erlenmeyer flask with 90 ml. of a sterile nutrient medium containing 1.0% corn steep liquor and 1.25% soybean powder—adjusted to pH 6.2—is inoculated with 10 ml. of the *Curvularia lunata* germination culture and shaken at 30° C. for 7 hours at 175 r.p.m. Then 0.6 ml. of a sterile solution of 30 mg. of 21-hydroxy-17α-methoxymethoxy-4-pregnene-3,20-dione in dimethylformamide is added to the culture, and the latter is further fermented for 65 hours under the above-described conditions.

The fermentation culture is worked up as set forth in Example 1(b), thus obtaining 27 mg. of 11β,21-dihydroxy-17α-methoxymethoxy-4-pregnene-3,20-dione, m.p. 180°-182° C.

(d) 2.5 g. of 11β,21-dihydroxy-17α-methoxymethoxy-4-pregnene-3,20-dione is dissolved in 40 ml. of anhydrous methylene chloride, cooled to 0° C., and combined within 15 minutes under argon with a solution of 2.25 ml. of titanium tetrachloride in 10 ml. of methylene chloride. The reaction mixture is thereafter stirred at room temperature for 90 minutes. Then, 150 ml. of methylene chloride and 100 ml. of saturated aqueous sodium bicarbonate solution are added thereto; the mixture is stirred for 15 minutes, the organic phase is separated, washed neutral, dried over sodium sulfate, and concentrated under vacuum. The residue is recrystallized from chloroform, thus obtaining 2.19 g. of 11β,17α,21-trihydroxy-4-pregnene-3,20-dione, decomposition point: 215° C.

EXAMPLE 2

(a) 50 g. of 3β,21-diacetoxy-17α-hydroxy-5-pregnen-20-one is combined with 50 mg. of anhydrous p-toluenesulfonic acid and 350 ml. of anhydrous methylene chloride, cooled to 0° C., and, after adding 10 g. of methylvinyl ether, stirred at 0° C. for 4 hours. Then triethylamine is added to the reaction mixture until a pH of 9 has been reached, and the mixture is concentrated under vacuum. Yield: 58 g. of 3β,21diacetoxy-17α-(1'-methoxyethoxy)-5-pregnen-20-one as a diastereomeric mixture, m.p. 80°-118° C. (A sample recrystallized from methanol melts at 132°-134° C.)

(b) Under the conditions of Example 1(b), a solution of 600 mg. of 3β,21-diacetoxy-17α-(1'-methoxyethoxy)-5-pregnen-20-one, mixture of diastereomers, in 5 ml. of dimethylformamide is reacted with a *Flavobacterium dehydrogenans* ATCC 13 930 culture and worked up, thus obtaining 394 mg. of 21-hydroxy-17α-(1'-methoxyethoxy)-4-pregnene-3,20-dione as a diastereomeric mixture, m.p. 166°-178° C.

(c) A solution of 100 mg. of 21-hydroxy-17α-(1'-methoxyethoxy)-4-pregnene-3,20-dione, diastereomeric mixture, in 2 ml. of dimethylformamide is fermented with a culture of *Curvularia lunata* NRRL 2380 under the conditions described in Example 1(c), then worked up, and the product is 105 mg. of 11β,21-dihydroxy-17α-(1'-methoxyethoxy)-4-pregnene-3,20-dione as an oily mixture of diastereomers.

This mixture is combined with 3 ml. of methanol and 0.5 ml. of 2 N aqueous hydrochloric acid and shaken for 5 hours at room temperature. Subsequently 4 ml. of water is added to the mixture, and the latter is neutralized with saturated aqueous sodium bicarbonate solution, extracted twice with respectively 8 ml. of ethylene chloride, the organic phase concentrated under vacuum, the residue purified by chromatograpy over an aluminum oxide column, and the yield is 69 mg. of 11β,17α,21-trihydroxy-4-pregnene-3,20-dione, m.p. 217°-219° C.

EXAMPLE 3

(a) 10.0 g. of 21-acetoxy-17α-hydroxy-4-pregnene-3,20-dione is combined with 13 mg. of anhydrous p-toluenesulfonic acid and 130 ml. of anhydrous methylene chloride, cooled to 0° C., and stirred, after adding 2.3 g. of methylvinyl ether, for 7 hours at 0° C. The reaction mixture is worked up as set forth in Example 2(a), thus obtaining 11.6 g. of 21-acetoxy-17α-(1'-methoxyethoxy)-4-pregnene-3,20-dione, m.p. 135°-150° C.

(b) A solution of 0.1 g. of 21-acetoxy-17α-(1'-methoxyethoxy)-4pregnene-3,20-dione, diastereomeric mixture, in 2 ml. of dimethylformamide is fermented with a culture of *Curvularia lunata* NRRL 2380 under the conditions described in Example 1(c), and then worked up. The thus-obtained 11β,21-dihydroxy-17α-(1'-methoxyethoxy)-4-pregnene-3,20-dione is then hydrolyzed under the conditions described in Example 2(c), thus obtaining 78 mg. of 11β,17α,21-trihydroxy-4-pregnene-3,20-dione, m.p. 217°-219° C.

EXAMPLE 4

(a) 10.0 g. of 21-acetoxy-17α-hydroxy-4-pregnene-3,20-dione is reacted, under the conditions described in Example 3(a), with 2.50 g. of ethylvinyl ether, worked up, and the product is 12.5 g. of 21-acetoxy-17α-(1'-ethoxyethoxy)-4-pregnene-3,20-dione in the form of an oily mixture of diastereomers.

(b) A solution of 0.1 g. of 21-acetoxy-17α-(1'-ethoxyethoxy)-4-pregnene-3,20-dione, diastereomeric mixture, in 2 ml. of dimethylformamide is hydroxylated with *Curvularia lunata* NRRL 2380 under the conditions described in Example 1(c), then worked up, and the product is 17α-(1'-ethoxyethoxy)-11β,21-dihydroxy-4-pregnene-3,20-dione; the latter is hydrolyzed under the conditions described in Example 2(c) to 63 mg. of 11β,17α,21-trihydroxy-4-pregnene-3,20-dione, m.p. 216°-217.5° C.

EXAMPLE 5

(a) 10.0 g. of 21-acetoxy-17α-hydroxy-4-pregnene-3,20-dione is reacted with 4.0 g. of isobutylvinyl ether under the conditions described in Example 3(a) and then worked up, thus obtaining 13.5 g. of 21-acetoxy-17α-(1'-isobutoxyethoxy)-4-pregnene-3,20-dione as an oily mixture of diastereomers.

(b) A solution of 0.1 g. of 21-acetoxy-17α-(1'-isobutoxyethoxy)-4-pregnene-3,20-dione, mixture of diastereomers, in 2 ml. of dimethylformamide is hydroxylated with *Curvularia lunata* NRRL 2380 under the conditions set forth in Example 1(c) and then worked up, thus producing 11β,21-dihydroxy-17α-(1'-isobutoxyethoxy)-4-pregnene-3,20-dione; the latter is saponified under the conditions indicated in Example 2(c) to 68 mg. of 11β,17α,21-trihydroxy-4-pregnene-3,20-dione, m.p. 214°–216° C. (decomposition).

EXAMPLE 6

(a) 1.95 g. of 21-acetoxy-17α-hydroxy-4-pregnene-3,20-dione is combined with 5 mg. of anhydrous p-toluenesulfonic acid, 25 ml. of anhydrous methylene chloride, and 3.5 ml. of dihyropyran and stirred for 13 hours at room temperature. The reaction mixture is worked up as set forth in Example 3(a), thus obtaining 2.0 g. of 21-acetoxy-17α-(2'-tetrahydropyranyloxy)-4-pregnene-3,20-dione as a diastereomeric mixture, m.p. 185°–200° C.

(b) A solution of 0.1 g. of 21-acetoxy-17α-(2'-tetrahydropyranyloxy)-4-pregnene-3,20 -dione, diastereomeric mixture, in 2 ml. of dimethylformamide is hydroxylated with *Curvularia lunata* NRRL 2380 under the conditions described in Example 1(c) and worked up, thus obtaining 11β,21-dihydroxy-17α-(2'-tetrahydropyranyloxy)-4-pregnene-3,20-dione; the latter is hydrolyzed under the conditions set forth in Example 2(c) to 72 mg. of 11β,17α,21-trihydroxy-4-pregnene-3,20-dione, m.p. 215° C. (decomposition).

EXAMPLE 7

(a) 50 g. of 21-acetoxy-17α-hydroxy-6α-methyl-4-pregnene-3,20-dione is reacted with 13.9 g. of methylvinyl ether under the conditions described in Example 3(a) and worked up, thus producing 59 g. of 21-acetoxy-17α-('-methoxyethoxy)-6α-methyl-4-pregnene-3,20-dione as an amorphous mass.

(b) A solution of 200 mg. of 21-acetoxy-17α-(1'-methoxyethoxy)-6α-methyl-4-pregnene-3,20-dione in 0.4 ml. of dimethylformamide is hydroxylated under the conditions described in Example 1(c) with *Curvularia lunata* NRRL 2380 and worked up, yielding 11β,21-dihydroxy-17α-(1'-methoxyethoxy)-6α-methyl-4-pregnene-3,20-dione which is hydrolyzed under the conditions set forth in Example 2(c) to 15 mg. of 11β,17α,21-trihydroxy-6α-methyl-4-pregnene-3,20-dione, m.p. 189°–192° C.

EXAMPLE 8

(a) 2.0 g. of 21-acetoxy-17α-hydroxy-16β-methyl-4-pregnene-3,20-dione is combined with 5 mg. of p-toluenesulfonic acid (anhydrous) and 25 ml. of anhydrous methylene chloride and cooled to 0° C. Then 0.5 g. of methylvinyl ether is added to the mixture under agitation, and the mixture is stirred for 5 hours at 0° C. and for another 12 hours at room temperature and then worked up as described in Example 3(a). Yield: 2.1 g. of 21-acetoxy-17α-(1'-methoxyethyl)-16β-methyl-4-pregnene-3,20-dione as an oily mixture of diastereomers.

(b) A solution of 50 mg. of 21-acetoxy-17α-(1'-methoxyethoxy)-16β-methyl-4-pregnene-3,20-dione, diastereomeric mixture, in 1 ml. of dimethylformamide is hydroxylated with *Curvularia lunata* NRRL 2380 under the conditions indicated in Example 1(c), thus obtaining 11β,21-dihydroxy-17α-(1'-methoxyethoxy)-16β-methyl-4-pregnene-3,20-dione which is hydrolyzed under the conditions described in Example 2(c) to 32 mg. of 11β,17α,21-trihydroxy-16β-methyl-4-pregnene-3,20-dione, m.p. 204°–207° C.

EXAMPLE 9

(a) 50 g. of 17α-hydroxy-4-pregnene-3,20-dione is reacted with 15 g. of methylvinyl ether under the conditions set forth in Example 3(a) and worked up, thus producing 51.2 g. of 17α-(1'-methoxyethoxy)-4-pregnene-3,20-dione, m.p. 115°–152° C.

(b) A solution of 0.1 g of 17α-(1'-methoxyethoxy)-4-pregnene-3,20-dione in 1 ml. of dimethylformamide is fermented under the conditions described in Example 1(c) with a culture of *Curvularia lunata* NRRL 2380 and worked up. The thus-obtained 11β-hydroxy-17α-(1'-methoxyethoxy)-4-pregnene-3,20 -dione (m.p. 85°–103° C.) is hydrolyzed under the conditions indicated in Example 2(c), thus obtaining 63 mg. of 11β,17α-dihydroxy-4-pregnene-3,20-dione, m.p. 222°–223.5° C.

EXAMPLE 10

(a) 50 g. of 3β,21-diacetoxy-17α-hydroxy-5-pregnen-20-one is reacted under the conditions described in Example 1(a) in 150 ml. of methylene chloride with 380 g. of formaldehyde bis-glycol monomethyl ether acetal, 50 g. of phosphorus pentoxide, and 100 g. of kieselguhr and worked up, thus obtaining 45.8 g. of 3β,21-diacetoxy-17α-(2'-methoxyethoxymethoxy)-5-pregnene-20-one, m.p. 160°–161° C.

(b) Under the conditions described in Example 1(b), 0.5 g. of 3β,21-diacetoxy-17α-(2'-methoxyethoxymethoxy)-5-pregnen-20-one is reacted with a culture of *Flavobacterium dehydrogenans* ATCC 13 930 and worked up. Yield: 390 mg. of 21-hydroxy-17α-(2'-methoxyethoxymethoxy)-4-pregnene-3,20-dione as a vitreous mass.

(c) Under the conditions of Example 1(c), 30 mg. of 21-hydroxy-17α-(2'-methoxyethoxymethoxy)-4-pregnene-3,20-dione is reacted with a culture of *Curvularia lunata* NRRL 2380 and worked up, thus producing 24 mg. of 11β,21-dihydroxy-17α-(2'-methoxyethoxymethoxy)-4-pregnene-3,20-dione, m.p. 143°–147° C.

(d) Under the conditions of Example 1(d), 10 mg. of 11β,21-dihydroxy-17α-(2'-methoxyethoxymethoxy)-4-pregnene-3,20-dione is reacted in 2 ml. of methylene chloride and 0.01 ml. of titanium tetrachloride and worked up, thus obtained 8 mg. of 11β,17α,21-trihydroxy-4-pregnene-3,20-dione, decomposition point 213° C.

EXAMPLE 11

A 2-liter Erlenmeyer flask with 500 ml. of a sterile nutrient solution containing 0.1% yeast extract
0.5% corn steep liquor
0.1% glucose
adjusted to pH 7.0 is inoculated with a supernatant broth of a dry culture of *Arthrobacter simplex* ATCC 6946 and shaken at 190 r.p.m. at 30° C. for 48 hours.

A 500-milliliter Erlenmayer flask with 90 ml. of the above-described nutrient medium is inoculated with 10 ml. of the *Arthrobacter simplex* germination culture and shaken at 30° C. for 6 hours at 165 r.p.m. Then 1 ml. of a sterile solution of 50 mg. of 11β,21-dihydroxy-17α-methoxymethoxy-4-pregnene-3,20-dione in dimethylformamide is added to the culture, and the latter is further fermented for 42 hours.

The fermentation culture is worked up as described in Example 1(b), thus obtaining 44.5 mg. of 11β,21-dihydroxy-17α-methoxymethoxy-1,4-pregnadiene-3,20-dione, m.p. 229°/230°–231° C.

EXAMPLE 12

A 2-liter Erlenmeyer flask with 500 ml. of a sterile nutrient solution containing 1% yeast extract (Difco)
0.45% disodium hydrogen phosphate
0.34% potassium hydrogen phosphate
0.2% "Tween" 80
adjusted to pH 6.7 is inoculated with a supernatant broth of a dry culture of *Nocardia globerula* ATCC 9356 and shaken at 30° C. for 72 hours at 190 r.p.m.

A 2-liter Erlenmeyer flask with 950 ml. of a sterile nutrient solution containing 2.0% corn steep liquor
0.3% diammonium hydrogen phosphate
0.25% "Tween" 80
adjusted to pH 6.5 is inoculated with 50 ml. of the Nocardia globerula germination culture and shaken at 30° C. for 24 hours at 190 r.p.m. Then 5 ml. of a sterile solution of 0.25 g. of 11β,21-dihydroxy-17α-(1'-methoxyethoxy)-6α-methyl-4-pregnene-3,20-dione in dimethylformamide is added to the culture, and the latter is fermented for another 72 hours. The fermentation culture is worked up as described in Example 1(b), thus obtaining 0.21 g. of 11β,21-dihydroxy-17α-(1'-methoxyethoxy)-6α-methyl-1,4-pregnadiene-3,20-dione, m.p. 173° C.

EXAMPLE 13

(a) 50 g. of 21-acetoxy-17α-hydroxy-4-pregnene-3,20-dione is suspended with 600 ml. of formaldehyde diethylacetal and 600 ml. of methylene chloride and cooled to −30° to −40° C. Under agitation, a mixture of 75 g. of phosphorus pentoxide and 150 g. of kieselguhr is introduced, and the mixture is stirred for 30 hours at −30° C. The solution is filtered and neutralized with triethylamine. After the solvents have been distilled off, the mixture is once more distilled off with methanol, and the residue is recrystallized from methanol, thus obtaining 35.9 g. of 21-acetoxy-17α-ethoxymethoxy-4-pregnene-3,20-dione which melts at 137°–139° C. after another recrystallization.

(b) A 2-liter Erlenmeyer flask with 1 l. of a sterile nutrient solution containing 1% corn steep liquor
1.25% soybean powder
adjusted to ph 6.2 is inoculated with a supernatant broth of a dry culture of *Curvularia lunata* NRRL 2380 and shaken at 30° C. for 72 hours at 175 r.p.m.

A 50-liter fermentor with 29 l. of a sterile nutrient medium as described above is inoculated with 1 l. of the *Curvularia lunata* germination culture and incubated for 24 hours at 30° C. under aeration with 2 m³ per hour.

A 50-liter fermentor with 36 l. of a sterile nutrient solution as described above is inoculated with 4 l. of the *Curvularia lunata* subculture and incubated for 10 hours at 30° C. under aeration with 2 m³ per hour and under agitation at 220 r.p.m. Then, 10 g. of 21-acetoxy-17α-ethoxymethoxy-4-pregnene-3,20-dione in 200 ml. of ethylene glycol monomethyl ether is added to the culture. Starting with the tenth hour, the pH value is maintained between 6.5 and 7.0. After another 4 hours, another 10 g. of 21-acetoxy-17α-ethoxymethoxy-4-pregnene-3,20-dione in 200 ml. of ethylene glycol monoethyl ether is added and the mixture is fermented for another 23 hours under the aforementioned conditions.

The fermentation culture is extracted three times with 10 l. of ethylene chloride and then worked up further as described in Example 1(b), thus obtaining 13.8 g. of 11β,21-dihydroxy-17α-ethoxymethoxy-4-pregnene-3,20-dione, m.p. 153°–154° C.

EXAMPLE 14

(a) 25 g. of 21-acetoxy-17α-hydroxy-4-pregnene-3,20-dione is suspended with 200 ml. of formaldehyde dipropylacetal and 320 ml. of methylene chloride and cooled to −20° C. Under agitation, a mixture of 49.3 g. of phosphorus pentoxide and 97 g. of kieselguhr is introduced, and the mixture is stirred for 22 hours at −20° C. The solution is filtered and neutralized with triethylamine. The methylene chloride is distilled off under vacuum, and the formaldehyde dipropylacetal phase is decanted from the separated oil. After additional solvent has been distilled off under vacuum, 19 g. of 21-acetoxy-17α-propoxymethoxy-4-pregnene-3,20-dione is crystallized, m.p. 145°–147° C.

(b) 10 g. of 21-acetoxy-17α-propoxymethoxy-4-pregnene-3,20-dione is ground with 1 g. of "Tween" 80 and three times the amount of water in a "Dyno" mill, type KDL (company: Bachofen, Basel). This ground substance is sterilized with 1% strength $H_2O_2$ for at least 4 hours.

*Curvularia lunata* NRRL 2380 is germinated as described in Example 13(b) in a shaken flask and a preliminary fermentor and then the main fermentor is inoculated with this culture. this fermentor is started as described in Example 13(b) and incubated for 10 hours in accordance with the conditions likewise set forth in Example 13(b). Then the ground material of 21-acetoxy-17α-propoxymethoxy-4-pregnene-3,20-dione is added to the culture and the fermentation is continued for another 44 hours, the pH value being maintained between 6.4 and 6.7. The fermentation culture is worked up as described in Example 13(b), thus obtaining 6.5 g. of 11β,21-dihydroxy-17α-propoxymethoxy-4-pregnene-3,20-dione, m.p. 134°/135°–136° C.

EXAMPLE 15

(a) 50 g. of 21-acetoxy-17α-hydroxy-4-pregnene-3,20-dione is suspended with 500 ml. of formaldehyde dibutylacetal and 500 ml. of methylene chloride and cooled to −35° C. Under agitation, a mixture of 74 g. of phosphorus pentoxide and 150 g. of kieselguhr is introduced, and the mixture is stirred for 30 hours at −35° C. The solution is filtered and neutralized with triethylamine. The methylene chloride is distilled off under vacuum and the formaldehyde dibutylacetal phase is decanted from the separated oil. After additional solvent has been distilled off under vacuum, 38.7 g. of 21- acetoxy-17α-butoxymethoxy-4-pregnene-3,20-dione is crystallized, m.p. 123.5°-124.5° C.

(b) 8 g. of 21-acetoxy-17α-butoxymethoxy-4-pregnene-3,20-dione is ground with 0.8 g. of "Tween" 80 as described in Example 14(b). *Curvularia lunata* NRRL 2380 is grown in a shaker flask as a germination culture, in a preliminary fermentor, and in a main fermentor, and fermented, as described in Example 13(b). After 10 hours of fermenting in the main fermentor, the substrate is added and the fermentation continued for another 50 hours.

The fermentation culture is worked up as described in Example 13(b), thus obtaining 3.7 g. of 11β,21-dihydroxy-17α-butoxymethoxy-4-pregnene-3,20-dione, m.p. 79°-81° C.

EXAMPLE 16

(a) 10.60 g. of 21-acetoxy-6α-fluoro-17α-hydroxy-4-pregnene-3,20-dione is dissolved in 265 ml. of methylene chloride and 47.7 ml. of formaldehyde dimethylacetal. A mixture of 7.95 g. of phosphorus pentoxide and 15.9 g. of kieselguhr is added in incremental portions, and the mixture is stirred for 90 minutes under nitrogen at room temperature. The solution is filtered and combined with 2.1 ml. of triethylamine. The solvents are distilled off and the residue recrystallized from methanol, thus obtaining 7.6 g. of 21-acetoxy-6α-fluoro-17α-methoxymethoxy-4-pregnene-3,20-dione, m.p. 161°-167° C.

(b) *Curvularia lunata* NRRL 2380 is grown as set forth in Example 13(b) in a shaker flask and in a preliminary and main fermentor. After 10 hours of fermentation in the main fermentor, 5 g. of 21-acetoxy-6α-fluoro-17α-methoxymethoxy-4-pregnene3,20-dione in 100 ml. of ethylene glycol monomethyl ether is added thereto. From this point in time, the pH is maintained at between 6.5 and 7.0. At the 14th hour another 5 g. of 21-acetoxy-6α-fluoro-17α-methoxymethoxy-4-pregnene-3,20-dione in 100 ml. of ethylene glycol monomethyl ether is added, and the fermentation is continued for another 26 hours.

The fermentation culture is worked up as described in Example 13(b), thus obtaining 4.2 g. of 11β,21-dihydroxy-6α-fluoro-17α-methoxymethoxy-4-pregnene-3,20-dione, m.p. 190°-192° C.

EXAMPLE 17

(a) 43 g. of 3β,21-diacetoxy-17α-hydroxy-16β-methyl-5-pregnene-20-one is dissolved in 800 ml. of formaldehyde dimethylacetal and cooled to −15° C. In incremental portions, a mixture of 43 g. of phosphorus pentoxide and 86 g. of kieselguhr is added; the mixture is stirred for 15 hours at about −15° C. The solution is filtered, neutralized with triethylamine, and the solvents are distilled off under vacuum. The residue is recrystallized with methanol, thus obtaining 31.5 g. of 3β,21-diacetoxy-17α-methoxymethoxy-16β-methyl-5-pregnen-20-one, m.p. 117°-118° C.

(b) *Flavobacterium dehydrogenans* ATCC 13 930 is germinated as described in Example 1(b) and fermented. At the 7th hour 4 ml. of a sterile solution of 0.2 g. of 3β,21-diacetoxy-17α-methoxymethoxy-16β-methyl-5-pregnen-20-one in dimethylformamide is added to the culture, and the latter is shaken for another 65 hours.

After fermentation has been completed, the culture is worked up as set forth in Example 1(b), thus obtaining 163 mg. of 21-hydroxy-17α-methoxymethoxy-16β-methyl-4-pregnene-3,20-dione, m.p. 126°/128-129° C.

(c) *Curvularia lunata* NRRL 2380 is germinated and fermented as set forth in Example 1(c). At the 7th hour, 1 ml. of a sterile solution of 50 mg. of 21-hydroxy-17α-methoxymethoxy-16α-methyl-4-pregnene-3,20-dione in dimethylformamide is added to the culture, and the latter is fermented for another 65 hours. The fermentation culture is worked up as described in Example 1(b), thus obtaining 34.5 mg. of 11β,21-dihydroxy-17α-methoxymethoxy-16β-methyl-4-pregnene-3,20-dione, m.p. 204°/205°-206° C.

EXAMPLE 18

3 g. of 11β,21-dihydroxy-17α-methoxymethoxy-4-pregnene-3,20-dione is combined in 20 ml. of pyridine with 5 ml. of acetic anhydride and stirred for 5 hours at room temperature. After precipitation into 200 ml. of ice water, the mixture is vacuum-filtered, thus obtaining 3.23 g. of 21-acetoxy-11β-hydroxy-17α-methoxymethoxy-4-pregnene-3,20-dione, m.p. 172°-177° C. after recrystallization from acetone.

EXAMPLE 19

4 g. of 11β,21-dihydroxy-17α-methoxymethoxy-4-pregnene-3,20-dione is combined in 25 ml. of pyridine with 8 ml. of propionic anhydride and stirred for 105 minutes at room temperature. After precipitation into 500 ml. of ice water, the mixture is stirred until the anhydride has been cleaved, then vacuum-filtered, and the yield is 4.43 g. of 11β-hydroxy-17α-methoxymethoxy-21-propionyloxy-4-pregnene-3,20-dione, m.p. 119°-121° C. after recrystallization from methanol.

EXAMPLE 20

4 g. of 11β,21-dihydroxy-17α-methoxymethoxy-4-pregnene-3,20-dione is combined in 25 ml. of pyridine with 9 ml. of butyric anhydride and stirred for 105 minutes at room temperature. After precipitation into 500 ml. of ice water, the mixture is stirred for another three hours and vacuum-filtered, thus obtaining 4.55 g. of 21-butyryloxy-11β-hydroxy-17α-methoxymethoxy-4-pregnene-3,20-dione which melts at 140°-142° C. after recrystallization from methanol.

EXAMPLE 21

4 g. of 11β,21-dihydroxy-17α-methoxymethoxy-4-pregnene-3,20-dione is combined in 25 ml. of pyridine with 11 ml. of trimethylacetic anhydride and 100 mg. of 4-dimethylaminopyridine. After six hours at room temperature, ice water is added, the mixture is extracted with methylene chloride, and this extract is washed with aqueous acetic acid, sodium bicarbonate solution, and water, dried with sodium sulfate, and the solvent distilled off under vacuum, thus obtaining 4.8 g. of 11β-hydroxy-17α-methoxymethoxy-21-trimethylacetoxy-4-pregnene-3,20-dione, m.p. 182°-184° C. after recrystallization from methanol.

EXAMPLE 22

5 g. of 11β,21-dihydroxy-17α-methoxymethoxy-1,4-pregnadiene-3,20-diode is combined in 30 ml. of pyridine with 8 ml. of acetic anhydride and stirred for 1.5 hours at room temperature. After precipitation into 300 ml. of ice water, the mixture is vacuum-filtered, thus obtaining 5.08 g. of 21-acetoxy-11β-hydroxy-17α-methoxymethoxy-1,4-pregnadiene-3,20-dione, m.p. 214° C. after recrystallization from methanol and a small amount of methylene chloride.

EXAMPLE 23

1 g. of 11β,21-dihydroxy-17α-methoxymethoxy-1,4-pregnadiene-3,20-dione is combined in 6 ml. of pyridine with 2 ml. of butyric anhydride and stirred for 1.5 hours at room temperature. After precipitation into ice water, the mixture is stirred for another two hours and then vacuum-filtered, thus obtaining 1.11 g. of 21-butyryloxy-11β-hydroxy-17α-methoxymethoxy-1,4-pregnadiene-3,20-dione, m.p. 182° C. after recrystallization from methanol with a small amount of methylene chloride.

EXAMPLE 24

0.32 g. of pyridine chlorochromate is combined with 2 ml. of anhydrous methylene chloride and then, under agitation, a solution of 0.45 g. of 21-acetoxy-11β-hydroxy-17α-methoxymethoxy-4-pregnene-3,20-dione in 7 ml. of methylene chloride is added thereto. After 4 hours at 20° C., the mixture is vacuum-filtered over kieselguhr, washed with methylene chloride/diethyl ether 1:1, and combined with a few drops of methanol. The solvent is distilled off under vacuum. The residue is combined with water under agitation and vacuum-filtered. Recrystallization from methanol yields 0.28 g. of 21-acetoxy-17α-methoxymethoxy-4-pregnene-3,11,20-trione, m.p. 160°–161° C.

EXAMPLE 25

6 g. of cortisone acetate is dissolved in 120 ml. of formaldehyde dimethylacetal and 120 ml. of methylene chloride and combined under ice cooling with a mixture of 12 g. of phosphorus pentoxide and 24 g. of kieselguhr. After 4.5 hours the mixture is filtered, neutralized with triethylamine, and the solvents are distilled off under vacuum. The residue is chromatographed on silica gel with toluene/ethyl acetate mixtures, thus obtaining 3.85 g. of 21-acetoxy-17α-methoxymethoxy-4-pregnene-3,11,20-trione, m.p. 160°–161° C. after recrystallization from methanol.

EXAMPLE 26

(a) 2 g. of 21-acetoxy-11β-hydroxy-17α-methoxymethoxy-4-pregnene-3,20-dione is dissolved in 20 ml. of pyridine and combined under ice cooling with 0.6 ml. of thionyl chloride. After 30 minutes the mixture is precipitated into ice water and vacuum-filtered, thus obtaining 1.76 g. of 21-acetoxy-17α-methoxymethoxy-4,9(11)-pregnadiene-3,20-dione, m.p. 194°–196° C. after recrystallization from methanol with a small amounts of methylene chloride.

(b) 5.0 g. of 21-acetoxy-17α-methoxymethoxy-4,9(11)-pregnadiene-3,20-dione is suspended in 50 ml. of tetrahydrofuran and combined at +20° C. with 20.56 ml. of 1N perchloric acid and 5.14 g. of N-bromosuccinimide. The mixture is stirred for another 15 minutes. The reaction mixture is precipitated into a solution of 5.14 g. of sodium sulfite and 350 ml. of ice water. The crystallized product is vacuum-filtered, washed neutral with water, and the still moist crystallized product is recrystallized from methanol/water, thus obtaining 5.0 g. of 21-acetoxy-9α-bromo-11β-hydroxy-17α-methoxymethoxy-4-pregnene-3,20-dione, m.p. 130°–131° C.

(c) 51.8 g. of 21-acetoxy-9α-bromo-11β-hydroxy-17α-methoxymethoxy-4-pregnene-3,20-dione is suspended in 518 ml. of ethanol and combined with 45.3 g. of anhydrous potassium acetate. The mixture is refluxed for one hour and after cooling to +20° C. precipitated into 5180 ml. of ice water. The crystallized product is vacuum-filtered, washed with water, and dried at +20° C. Yield: 41.75 g. of 21-acetoxy-9β,11β-epoxy-17α-methoxymethoxy-4-pregnene-3,20-dione, m.p. 138°–139.5° C. after recrystallization from methanol.

(d) 1.0 g. of 21-acetoxy-9β,11β-epoxy-17α-methoxymethoxy-4-pregnene-3,20-dione is dissolved in 10 ml. of methylene chloride and cooled with ice water. Gaseous hydrochloric acid dried over sulfuric acid is introduced in a gradual stream until no starting material can be found any longer in a thin-layer chromatogram. The reaction mixture is precipitated into 120 ml. of 1% sodium bicarbonate solution. The methylene chloride phase is separated, washed neutral with water, dried, and concentrated to dryness, thus obtaining 1.1 g. of 21-acetoxy-9α-chloro-11β-hydroxy-17α-methoxymethoxy-4-pregnene-3,20-dione, m.p. 194.5° C. after recrystallization.

EXAMPLE 27

5.0 g. of 21-acetoxy-17α-methoxymethoxy-4,9(11)-pregnadiene-3,20-dione is suspended in 50 ml. of tetrahydrofuran and combined at +20° C. with 20.56 ml. of 1N perchloric acid and 2.78 g. of N-chlorosuccinimide. The mixture is stirred for 24 hours, adding another 3.52 ml. of 70% perchloric acid. The reaction mixture is precipitated into a solution of 5.14 g. of sodium sulfite and 350 ml. of ice water. The crystallized product is vacuum-filtered, washed neutral with water, and the moist crystallized product is recrystallized from methanol/water. Yield: 1.5 g. of 21-acetoxy-9α-chloro-11β-hydroxy-17α-methoxymethoxy-4-pregnene-3,20-dione, m.p. 189°–192° C. after crystallization from ethyl acetate and acetone.

EXAMPLE 28

10 g. of 9α-fluorohydrocortisone acetate is dissolved in 67.4 ml. of methylene chloride and 134.8 ml. of methylal and cooled with an ice-methanol bath. 10 g. of phosphorus pentoxide, mixed with 20 g. of kiselguhr, is introduced into this solution, and the latter is stirred at −15° C. for 5 hours. The solution is filtered and neutralized with triethylamine. After the solvent has been distilled, the mixture is once again distilled off with methanol and the residue is crystallized from methanol. By chromatography on silica gel with methylene chloride and 5% methanol, the products are separated, thus obtaining 3.28 g. of 21-acetoxy-9α-fluoro-11β,17α-dimethoxymethoxy-4-pregnene-3,20-dione, m.p. 132°–134° C.; 0.56 g. of 21-acetoxy-9α-fluoro-11β-hydroxy-17α-methoxymethoxy-4-pregnene-3,20-dione, m.p. 211°–214° C.; and 0.79 g. of 21-acetoxy-9α-fluoro-17α-hydroxy-11β-methoxymethoxy-4-pregnene-3,20-dione, m.p. 196°–199° C.

EXAMPLE 29

5.0 g. of 21-acetoxy-9α-chloro-11β-hydroxy-17α-methoxymethoxy-4-pregnene-3,20-dione is suspended in 10 ml. of methylene chloride and 20 ml. of methanol and cooled to +3° C. Within 5 minutes, a solution of 0.31 g. of potassium hydroxide in 11 ml. of methanol is added dropwise and the mixture stirred for another 80 minutes. The reaction mixture is neutralized with 0.34 ml. of glacial acetic acid and precipitated into 350 ml. of water. The crystallized product is vacuum-filtered and dried, thus obtaining 2.32 g. of 9α-chloro-11β,21-dihydroxy-17α-methoxymethoxy-4-pregnene-3,20-dione, m.p. 188°–189° C. after recrystallization from methanol/methylene chloride.

EXAMPLE 30

(a) A solution of 5.0 g. of prednisolone 21-acetate in 25 ml. of pyridine is combined at −15° C. dropwise with 3 ml. of trifluoroacetic anhydride and stirred for 10 minutes at −10° C. The mixture is poured into an ice water/sodium chloride solution and the precipitate is filtered off. The residue is taken up in methylene chloride, washed neutral, and concentrated under vacuum after drying over sodium sulfate. Yield: 6.3 g. of 21-acetoxy-17α-hydroxy-11β-trifluoroacetoxy-1,4-pregnadiene-3,20-dione.

(b) 3.0 g. of the above crude product is stirred overnight in a mixture of 25 ml. of dimethyl sulfoxide, 15 ml. of acetic anhydride, and 4.8 ml. of glacial acetic acid at room temperature. The reaction solution is poured onto a 10% sodium carbonate solution, and the precipitate is filtered off. The residue is dissolved in methylene chloride and worked up, after washing the mixture neutral, as usual. After chromatography on 350 mg. of silica gel with a methylene chloride/acetone gradient (0–8% acetone), 2.83 g. of 21-acetoxy-17α-methylthiomethoxy-11β-trifluoroacetoxy-1,4-pregnadiene-3,20-dione is isolated.

(c) 1.5 g. of 21-acetoxy-17α-methylthiomethoxy-11β-trifluoroacetoxy-1,4-pregnadiene-3,20-dione is stirred in 38 ml. of methanol and 1.9 ml. of triethylamine for 4 hours at room temperature. The crude product is purified on 300 g. of silica gel with a methylene chloride/acetone gradient (0–8% acetone), thus isolating 1.2 g. of 21-acetoxy-11β-hydroxy-17α-methylthiomethoxy-1,4-pregnadiene-3,20-dione, m.p. 155° C.

EXAMPLE 31

(a) 20.0 g. of 21-acetoxy-9α-fluoro-11β,17α-dihydroxy-4-pregnene-3,20-dione is reacted analogously to Example 30(a) with trifluoroacetic anhydride to 23.6 g. of 21-acetoxy-9α-fluoro-17α-hydroxy-11β-trifluoroacetoxy-4-pregnene-3,20-dione.

(b) 3.0 g. of the above crude product is treated analogously to Example 30(b) with dimethyl sulfoxide, acetic anhydride, and glacial acetic acid. The crude product is purified on 300 g. of silica gel with a methylene chloride/acetone gradient (0–8% acetone). Yield: 2.58 g. of 21-acetoxy-9α-fluoro-17α-methylthiomethoxy-11β-trifluoroacetoxy-4-pregnene-3,20-dione.

(c) 21-acetoxy-9α-fluoro-17α-methylthiomethoxy-11β-trifluoroacetoxy-4-pregnene-3,20-dione is reacted in 28 ml. of methaol with 1.4 ml. of triethylamine analogously to Example 30(c), and the crude product is purified on 100 g. of silica gel with a methylene chloride/acetone gradient (0–12% acetone). Yield: 914 mg. of 21-acetoxy-9α-fluoro-11β-hydroxy-17α-methylthiomethoxy-4-pregnene-3,20-dione, m.p. 193° C.

EXAMPLE 32

(a) A suspension of 6.0 g. of 21-acetoxy-17α-hydroxy-1,4,9-pregnatriene-3,20-dione in 46 ml. of anhydrous acetonitrile is combined with 11.5 ml. of methoxyethoxymethyl chloride and 11.5 ml. of diisopropylethylamine and stirred for 7.5 hours at 30° C. After precipitation into ice water, the vacuum-filtered precipitate is dissolved in methylene chloride, washed neutral, and concentrated after drying. The purification of the reaction product takes place on 800 g. of silica gel with a hexane/ethyl acetate gradient (0–30% ethyl acetate).

Yield: 4.9 g. of 21-acetoxy-17α-(1,3,6-trioxaheptyl)-1,4,9-pregnatriene-3,20-dione, m.p. 140° C.

(b) A solution of 1.0 g. of 21-acetoxy-17α-(1,3,6-trioxaheptyl)-1,4,9-pregnatriene-3,20-dione in 10 ml. of dioxane is combined with 900 mg. of N-chlorosuccinimide and 5 ml. of a 10% perchloric acid. The mixture is stirred for 3.5 hours at room temperature and poured into an ice water-sodium chloride-sodium hydrogen sulfate solution. The mixture is filtered off and the residue taken up in methylene chloride, washed neutral, and concentrated after drying over sodium sulfate. The crude product is purified on 100 g. of silica gel with a methylene chloride/acetone gradient (0–15% acetone). Yield: 760 mg. of 21-acetoxy-9α-chloro-11β-hydroxy-17α-(1,3,6-trioxaheptyl)-1,4-pregnadiene-3,20-dione (m.p. 204° C.), as well as 180 mg. of 21-acetoxy-9α,11β-dichloro-17α-(1,3,6-trioxaheptyl)-1,4-pregnadiene-3,20-dione (m.p. 148° C.).

EXAMPLE 33

(a) 4.0 g. of 21-acetoxy-17α-hydroxy-1,4,9-pregnatriene-3,20-dione is dissolved in 28 ml. of anhydrous methylene chloride and 18 ml. of formaldehyde dimethylacetal and combined in incremental portions with a mixture of 6.0 g. of kieselguhr W 20 and 3.0 g. of phosphorus pentoxide. The mixture is stirred for 45 minutes at room temperature, vacuum-filtered, and the residue eluted once again with methylene chloride containing 3–5% triethylamine. The crude product is purified on 750 g. of silica gel with a methylene chloride/acetone gradient (0–12% acetone). Yield: 3.3 g. of 21-acetoxy-17α-methoxymethoxy-1,4,9-pregnatriene-3,20-dione, m.p. 160° C.

(b) 1.6 g. of 21-acetoxy-17α-methoxymethoxy-1,4,9-pregnatriene-3,20-dione is dissolved in 16 ml. of dioxane and combined with 1.5 g. of N-chlorosuccinimide. After the dropwise addition of 8 ml. of 10% aqueous perchloric acid, the mixture is stirred for 3 hours at room temperature and poured onto an ice water-sodium chloride-sodium bisulfite solution. The mixture is filtered off and worked up analogously to Example 2. The crude product is purified on 175 g. of silica gel with a methylene chloride/acetone gradient (0–12% acetone). Yield: 1.1 g. of 21-acetoxy-9α-chloro-11β-hydroxy-17α-methoxymethoxy-1,4-pregnadiene-3,20-dione (m.p. 224° C.) and 250 mg. of 21-acetoxy-9α,11β-dichloro-17α-methoxymethoxy-1,4-pregnadiene-3,20-dione (m.p. 162° C.).

EXAMPLE 34

(a) 1.8 g. of 21-acetoxy-17α-(1,3,6-trioxaheptyl)-1,4,9-pregnatriene-3,20-dione is dissolved in 18 ml. of dioxane and combined with 1.6 g. of N-bromosuccinimide. After the dropwise addition of 8.5 ml. of 10% aqueous perchloric acid, the mixture is stirred for 30 minutes at room temperature and introduced into an ice water-sodium chloride-sodium bisulfite solution. The mixture is worked up analogously to Example 5. Yield: 2.3 g. of crude 21-acetoxy-9α-bromo-11β-hydroxy-17α-(1,3,6-trioxaheptyl)-1,4-pregnadiene-3,20-dione.

(b) 2.0 g. of the above crude product is dissolved in 20 ml. of hexamethylphosphoric triamide and stirred with 2.4 g. of lithium chloride for 0.5 hour at a bath temperature of 80° C. After ice water-sodium chloride precipitation, the mixture is filtered off and worked up as usual. The crude product is purified on 350 g. of silica gel with a methylene chloride/acetone gradient (0–15% acetone). Yield: 570 mg. of 21-acetoxy-11β-hydroxy-17α-

(1,3,6-trioxaheptyl)-1,4,8-pregnatriene-3,20-dione, m.p. 170° C.

EXAMPLE 35

(a) 3.2 g. of tris-triphenylphosphine rhodium(I) chloride is dissolved in a mixture of 100 ml. of methanol and 300 ml. of benzene and preliminarily hydrogenated for 1.5 hours. After the addition of 4.0 g. of 21-acetoxy-17α-methoxymethoxy-1,4,9-pregnatriene-3,20-dione, the mixture is hydrogenated for 6.5 hours under normal pressure. The solution is concentrated on a forced circulation evaporator and the residue is purified on 400 g. of silica gel with a methylene chloride/acetone gradient (0–12% acetone). Yield: 2.1 g. of 21-acetoxy-17α-methoxymethoxy-4,9-pregnadiene-3,20-dione.

(b) Analogously to Example 33(b), 1.1 g. of 21-acetoxy-17α-methoxymethoxy-4,9-pregnadiene-3,20-dione is treated with N-chlorosuccinimide and perchloric acid. After purification, 430 mg. of 21-acetoxy-9α-chloro-11β-hydroxy-17≢-methoxymethoxy-4-pregnene-3,20-dione is isolated, m.p. 195° C.

EXAMPLE 36

(a) 17.5 g. of 21-chloro-17α-hydroxy-4,9-pregnadiene-3,20-dione is reacted analogously to Example 33(a) with 236 ml. of formaldehyde dimethylacetal and worked up. The crude product is purified on 2.25 kg. of silica gel with a methylene chloride/acetone gradient (0–4% acetone). Yield: 7.6 g. of 21-chloro-17α-methoxymethoxy-4,9-pregnadiene-3,20-dione, m.p. 152° C.

(b) 1.8 g. of 21-chloro-17α-methoxymethoxy-4,9-pregnadiene-3,20-dione is treated analogously to Example 33(b) with N-chlorosuccinimide and perchloric acid. The crude product is purified on 100 g. of silica gel with a methylene chloride/acetone gradient (0–10% acetone), thus isolating 126 mg. of 9α,21-dichloro-11β-hydroxy-17α-methoxymethoxy-4pregnene-3,20-dione, m.p. 197° C. (decomposition).

EXAMPLE 37

(a) 3.0 g. of 21-fluoro-17α-hydroxy-1,4,9-pregnatriene-3,20-dione is reacted analogously to Example 33(a) with 14 ml. of formaldehyde dimethylacetal and the mixture is worked up under the conditions set forth in Example 4. The crude produt is purified on 450 g. of silica gel with a methylene chloride/acetone gradient (0–8% acetone). Yield: 1.5 g. of 21-fluoro-17α-methoxymethoxy-1,4,9-pregnatriene-3,20-dione.

(b) Under the conditions of Example 33(b), 500 mg. of 21-fluoro-17α-methoxymethoxy-1,4,9-pregnatriene-3,20-dione is reacted with N-chlorosuccinimide and perchloric acid. After working the mixture up as described above and purification on silica gel, 420 mg. of 9α-chloro-21-fluoro-11β-hydroxy-17α-methoxymethoxy-1,4-pregnadiene-3,20-dione is isolated, m.p. 245° C.

EXAMPLE 38

(a) 1.0 g. of 17α-hydroxy-1,4,9-pregnatriene-3,20-dione is reacted under the conditions of Example 33(a) with formaldehyde dimethylacetal, thus isolating 823 mg. of 17α-methoxymethoxy-1,4,9-pregnatriene-3,20-dione as the crude product.

(b) 823 mg. of the above crude product is treated analogously to Example 33(b) with N-chlorosuccinimide and perchloric acid and worked up under the conditions described therein and purified. Yield: 410 mg. of 9α-chloro-11β-hydroxy-17α-methoxymethoxy-1,4-pregnadiene-3,20-dione, m.p. 227° C.

EXAMPLE 39

(a) Analogously to Example 34(a), 1.0 g. of 21-fluoro-17α-methoxymethoxy-1,4,9-pregnatriene-3,20-dione is treated with 900 mg. of N-bromosuccinimide and 5 ml. of a 10% aqueous perchloric acid, thus isolating 1.1 g. of 9α-bromo-21-fluoro-11β-hydroxy-17α-methoxymethoxy-1,4-pregnadiene-3,20-dione.

(b) 1.1 g. of the crude 9α-bromo-21-fluoro-11β-hydroxy-17α-methoxymethoxy-1,4-pregnadiene-3,20-dione is reacted with 1.4 g. of lithium chloride analogously to Example 34(b) to 21-fluoro-11β-hydroxy-17α-methoxymethoxy-1,4,8-pregnatriene-3,20-dione. Yield: 490 mg., m.p. 218° C.

EXAMPLE 40

(a) 3.3 g. of 21-chloro-17α-hydroxy-1,4,9-pregnatriene-3,20-dione is reacted under the conditions of Example 33(a) with formadehyde dimethylacetal, thus isolating 2.4 g. of 21-chloro-17α-methoxymethoxy-1,4,9-pregnatriene-3,20-dione.

(b) 1.4 g. of 21-chloro-17α-methoxymethoxy-1,4,9-pregnatriene-3,20-dione is treated with N-bromosuccinimide analogously to Example 34(a), thus isolating 1.7 g. of 9α-bromo-21-chloro-11β-hydroxy-17α-methoxymethoxy-1,4-pregnadiene-3,20-dione as the crude product.

(c) Under the conditions of Example 34(b), 1.7 g. of 9α-bromo-21-chloro-11β-hydroxy-17α-methoxymethoxy-1,4-pregnadiene-3,20-dione is reacted with 2.1 g. of lithium chloride. The crude product is purified on 300 g. of silica gel with a methylene chloride/acetone gradient (0–8% acetone). Yield: 530 mg. of 21-chloro-11β-hydroxy-17α-methoxymethoxy-1,4,8-pregnatriene-3,20-dione, m.p. 166° C.

EXAMPLE 41

(a) Analogously to Example 38, 3.4 g. of 21-fluoro-17α-methoxymethoxy-4,9-pregnadiene-3,20-dione is produced from 7.6 g. of 21-fluoro-17α-hydroxy-4,9-pregnadiene-3,20-dione and 68 ml. of formaldehyde dimethylacetal.

(b) Under the conditions of Example 36(b), 1.4 g. of 21-fluoro-17α-methoxymethoxy-4,9-pregnadiene-3,20-dione is treated with N-chlorosuccinimide and perchloric acid. The crude product is purified on 100 g. of silica gel with a methylene chloride/acetone gradient (0–10% acetone). Yield: 380 mg. of 9α-chloro-21-fluoro-11β-hydroxy-17α-methoxymethoxy-4-pregnene-3,20-dione, m.p. 214° C. (decomposition).

EXAMPLE 42

(a) At −10° C., 20.0 g. of 9α-fluoro-11β,17α-dihydroxy-21-propionyloxy-1,4-pregnadiene-3,20-dione is introduced into a mixture of 100 ml. of pyridine and 12 ml. of trifluoroacetic anhydride. The mixture is stirred for 10 minutes at −10° C. After preparation into ice water, the mixture is filtered off and the residue taken up in methylene chloride. After washing and drying of the organic solution, the latter is concentrated under vacuum, thus isolating 22.0 g. of 9α-fluoro-17α-hydroxy-21-propionyloxy-11β-trifluoroacetoxy-1,4-pregnadiene -3,20-dione.

(b) 22.0 g. of the above crude product is reacted under the conditions of Example 33(a) with 90 ml. of formaldehyde dimethylacetal, thus isolating 9α-fluoro- 17α-methoxymethoxy-21-propionyloxy-11α-trifluoroacetoxy-1,4-pregnadiene-3,20-dione as a crude product.

(c) The crude 9α-fluoro-17α-methoxymethoxy-21-propionyloxy-11β-trifluoroacetoxy-1,4-pregnadiene-3,20-dione is dissolved in 500 ml. of methanol and, after adding 25 ml. of triethylamine, the mixture is stirred for 30 minutes at room temperature. The reaction solution is then concentrated to dryness under vacuum and the residue chromatographed on 2.25 kg. of silica gel with a methylene chloride/acetone gradient (0–12% acetone). Yield: 12.3 g. of 9α-fluoro-11β-hydroxy-17α-methoxymethoxy-21-propionyloxy-1,4-pregnadiene-3,20-dione, m.p. 241° C.

EXAMPLE 43

(a) Under the conditions of Example 42(a), 1.0 g. of 21-butyryloxy-9α-fluoro-11β,17α-dihydroxy-1,4-pregnadiene-3,20-dione is reacted with trifluoroacetic anhydride and then worked up, thus isolating 0.9 g. of 21-butyryloxy-9α-fluoro-17α-hydroxy-11β-trifluoroacetoxy-1,4-pregnadiene-3,20-dione.

(b) 800 mg. of the above crude product is treated analogously to Example 42(b) with 3.6 ml. of formaldehyde dimethylacetal. After the mixture has been worked up, the yield is 1.1 g. of crude 21-butyryloxy-9α-fluoro-17α-methoxymethoxy-11α-trifluoroacetoxy-1,4-pregnadiene-3,20-dione.

(c) 1.1 g. of crude 21-butyryloxy-9α-fluoro-17α-methoxymethoxy-11β-trifluoroacetoxy-1,4-pregnadiene-3,20-dione is reacted analogously to Example 42(b) with triethylamine. The crude product is chromatographed on 75 g. of silica gel with a methylene chloride/acetone gradient (0–15% acetone). Yield: 540 mg. of 21-butyryloxy-9α-fluoro-11β-hydroxy-17α-methoxymethoxy-1,4-pregnadiene-3,20-dione, m.p. 247° C.

EXAMPLE 44

2.0 g. of 21-butyryloxy-9α-fluoro-17α-hydroxy-1,4-pregnadiene-3,11,20-trione is reacted analogously to Example 33(a) with 9 ml. of formaldehyde dimethylacetal and worked up. The crude product is purified on 300 g. of silica gel with a methylene chloride/acetone gradient (0–10% acetone). Yield: 2.07 g. of 21-butyryloxy-9α-fluoro-17α-methoxymethoxy-1,4-pregnadiene-3,11,20-trione, m.p. 192° C.

EXAMPLE 45

Analogously to Example 32, 700 mg. of 21-butyryloxy-9α-fluoro-17α-hydroxy-1,4-pregnadiene-3,11,20-trione is reacted with 1.54 ml. of methoxyethoxymethyl chloride. The crude product is purified on 135 g. of silica gel with a methylene chloride/acetone gradient (0–5% acetone). Yield: 430 mg. of 21-butyryloxy-9α-fluoro-17α-(1,3,6-trioxaheptyl)-1,4-pregnadiene-3,11,20-trione, m.p. 126° C.

EXAMPLE 46

(a) 15.2 g. of 9α-fluoro-11β,17α-dihydroxy-16β-methyl-21-propionyloxy-1,4-pregnadiene-3,20-dione (prepared from 9α-fluoro-11α,17α,21-trihydroxy-16α-methyl-1,4-pregnadiene-3,20-dione and propionic anhydride) is treated with 9.1 ml. of trifluoroacetic anhydride analogously to Example 42(a), thus obtaining 15.4 g. of 9α-fluoro-17β-hydroxy-16β-methyl-21-propionyloxy-11β-trifluoroacetoxy-1,4-pregnadiene-3,20-dione.

(b) 15.4 g. of the above crude product is reacted under the conditions of Example 42(b) with formaldehyde dimethylacetal to 9α-fluoro-17α-methoxymethoxy-16β-methyl-21-propionyloxy-11β-trifluoroacetoxy-1,4-pregnadiene-3,20-dione; yield: 16.9 g. of the crude product.

(c) A solution of the crude 9α-fluoro-17α-methoxymethyl-16β-methyl-21-propionyloxy-11β-trifluoroacetoxy-1,4-pregnadiene-3,20-dione in 250 ml. of methanol is treated analogously to Example 42(c) with 30 ml. of triethylamine. After the mixture has been worked up, the crude product is purified on 1.5 kg. of silica gel with a methylene chloride/acetone gradient (0–10% acetone). Yield: 9.6 g. of 9α-fluoro-11β-hydroxy-17α-methoxymethoxy-16β-methyl-21-propionyloxy-1,4-pregnadiene-3,20-dione, m.p. 169° C.

EXAMPLE 47

600 mg. of 9α-fluoro-11β-hydroxy-17α-methoxymethoxy-16β-methyl-21-propionyloxy-1,4-pregnadiene-3,20-dione is hydrogenated with 500 mg. of tris-triphenylphosphine rhodium(I) chloride under the conditions of Example 35(a) and then worked up. After the crude product has been chromatographed on 65 g. of silica gel with a methylene chloride/acetone gradient (0–10% acetone), 347 mg. of 9α-fluoro-11β-hydroxy-17α-methoxymethoxy-16β-methyl-21-propionyloxy-4-pregnene-3,20-dione is isolated, m.p. 165° C.

EXAMPLE 48

A suspension of 6.9 g. of 9α-fluoro-11β-hydroxy-17α-methoxymethoxy-16β-methyl-21-propionyloxy-1,4-pregnadiene-3,20-dione in 80 ml. of methanolic 0.2 N potassium hydroxide solution is stirred for 45 minutes at 0° C. The mixture is neutralized with 10% acetic acid. After precipitation into ice water and working up of the reaction mixture, a crude product is obtained which is purified on 450 g. of silica gel with a methylene chloride/acetone gradient (0–20% acetone). Yield: 4.1 g. of 9α-fluoro-11β,21-dihydroxy-17α-methoxymethoxy-16β-methyl-1,4-pregnadiene-3,20-dione, m.p. 220° C.

EXAMPLE 49

(a) A solution of 1.7 g. of 9α-fluoro-11β,21-dihydroxy-17α-methoxymethoxy-16β-methyl-1,4-pregnadiene-3,20-dione in 17 ml. of pyridine is stirred with 2.04 g. of tosyl chloride for 1 hour at room temperature. After precipitation into ice water, the precipitate is taken up in methylene chloride and worked up as usual. The crude product is purified on 135 g. of silica gel with a methylene chloride/acetone gradient (0–10% acetone). Yield: 876 mg. of 9α-fluoro-11β-hydroxy-17α-methoxymethoxy-16β-methyl-21-tosyloxy-1,4-pregnadiene-3,20-dione.

(b) 876 mg. of the above product is stirred in 17 ml. of hexamethylphosphoric triamide with 880 mg. of lithium chloride for 1 hour at 80° C. The mixture is poured onto ice water and the precipitate filtered off. After working up the reaction mixture, the crude product is recrystallized from hexane/acetone. Yield: 485 mg. of 21-chloro-9α-fluoro-11β-hydroxy-17α-methoxymethoxy-16β-methyl-1,4-pregnadiene-3,20-dione, m.p. 204° C.

EXAMPLE 50

(a) A suspension of 11.2 g. of 9α-fluoro-11β-hydroxy-17α-methoxymethoxy-21-propionyloxy-1,4-pregnadiene-3,20-dione is combined with 129 ml. of a methanolic 0.2 N potassium hydroxide solution. The mixture is stirred for 1 hour at room temperature and worked up as described in Example 48. After chromatography on 1.5 kg. of silica gel with a methylene chloride/acetone gradient (0–35% acetone), 7.5 g. of 9α-fluoro-11β,21-dihydroxy-17α-methoxymethoxy-1,4-pregnadiene-3,20-dione is isolated.

(b) Analogously to Example 49(a), 1.0 g. of the above crude product is reacted with 2.0 g. of tosyl chloride. The crude product is purified on 200 g. of silica gel with a methylene chloride/acetone gradient (0–10% acetone). Yield: 886 mg. of 9α-fluoro-11β-hydroxy-17α-methoxymethoxy-21-tosyloxy-1,4-pregnadiene-3,20-dione.

(c) 886 mg. of 9α-fluoro-11β-hydroxy-17α-methoxymethoxy-21-tosyloxy-1,4-pregnadiene-3,20-dione is treated under the conditions of Example 49(b) with lithium chloride and worked up. Purification is effected by recrystallization from acetone/hexane. Yield: 392 mg. of 21-chloro-9α-fluoro-11β-hydroxy-17α-methoxymethoxy-1,4-pregnadiene-3,20-dione, m.p. 225° C.

EXAMPLE 51

(a) 20.0 g. of 21-acetoxy-9α-fluoro-11β,17-dihydroxy-4-pregnene-3,20-dione is reacted analogously to Example 42(a) with 12 ml. of trifluoroacetic anhydride to 21-acetoxy-9α-fluoro-17α-hydroxy-11β-trifluoroacetoxy-4-pregnene-3,20-dione.

(b) 5.0 g. of the above crude product is converted analogously to Example 33(a) with 22.5 ml. of formaldehyde dimethylacetal into 21-acetoxy-9α-fluoro-17α-methoxymethoxy-11β-trifluoroacetoxy-4-pregnene-3,20-dione; yield: 5.3 g.

(c) 5.3 g. of 21-acetoxy-9α-fluoro-17α-methoxymethoxy-11β-trifluoroacetoxy-4-pregnene-3,20-dione is treated analogously to Example 42(c) with triethylamine. The crude product is purified on 500 g. of silica gel with a methylene chloride/acetone gradient (0–8% acetone). Yield: 560 mg. of 21-acetoxy-9α-fluoro-11β-hydroxy-17α-methoxymethoxy-4-pregnene-3,20-dione, m.p. 213° C.

EXAMPLE 52

1.0 g. of 21-butyryloxy-9α-fluoro-11β-hydroxy-17α-methoxymethoxy-1,4-pregnadiene-3,20-dione is hydrogenated with 800 mg. of tris-triphenylphosphine rhodium(I) chloride under the conditions of Example 35(a) and worked up. After chromatography of the crude product on 100 g. of silica gel with a methylene chloride/acetone gradient (0–10% acetone), 620 mg. of 21-butyryloxy-9α-fluoro-11β-hydroxy-17α-methoxymethoxy-4-pregnene-3,20-dione, m.p. 183° C., is isolated.

EXAMPLE 53

(a) Analogously to Example 48, 28.0 g. of 21-acetoxy-9α-fluoro-11β-hydroxy-17α-methoxymethoxy-4-pregnene-3,20-dione is saponified with methanolic 0.2 N potassium hydroxide solution to 9α-fluoro-11β,21-dihydroxy-17α-methoxymethoxy-4-pregnene-3,20-dione.

(b) A solution of 500 mg. of 9α-fluoro-11β,21-dihydroxy-17α-methoxymethoxy-4-pregnene-3,20-dione in 5 ml. of pyridine is stirred with 7.5 ml. of n-valeric anhydride for 1 hour at room temperature. After ice water precipitation, the mixture is filtered off and worked up as usual. The crude product is purified on 400 g. of silica gel with a hexane/ethyl acetate gradient (0–30% ethyl acetate). Yield: 235 mg. of 9α-fluoro-11β-hydroxy-17α-methoxymethoxy-21-valeryloxy-4-pregnene-3,20-dione, m.p. 181° C.

EXAMPLE 54

(a) 29.1 g. of 21-acetoxy-6-chloro-17α-hydroxy-4,6-pregnadiene-3,20-dione is dissolved in 730 ml. of methylene chloride and 131.0 ml. of formaldehyde dimethylacetal. A mixture of 22.12 g. of phosphorus pentoxide and 44 g. of kieselguhr is added in incremental portions, and the mixture is stirred for 2.5 hours under nitrogen at room temperature. The solution is filtered and combined with 5.8 ml. of triethylamine. The solvents are distilled off, and the residue is recrystallized from methanol with the addition of activated carbon and 1% triethylamine, thus obtaining 15.6 g. of 21-acetoxy-6-chloro-17α-methoxymethoxy-4,6-pregnadiene-3,20-dione, m.p. 183°–186° C.

(b) *Curvularia lunata* NRRL 2380 is grown—as described in Example 13(b)—in a shaker flask, a preliminary fermentor, and a main fermentor. At the tenth hour in the main fermentor, 3 g. of 21-acetoxy-6-chloro-17α-methoxymethoxy-4,6-pregnadiene-3,20-dione is added in 60 ml. of ethylene glycol monomethyl ether. The pH value is maintained, starting with this point in time, at between 6.4 and 6.7, and fermentation is continued for another 20 hours. The fermentation culture is worked up—as described in Example 13(b)—thus obtaining 1.8 g. of 11β,21-dihydroxy-6-chloro-17α-methoxymethoxy-4,6-pregnadiene-3,20-dione, m.p. 234°/235°–236° C.

EXAMPLE 55

(a) 38.85 g. of 21-acetoxy-17α-hydroxy-4-pregnene-3,20-dione is stirred together with 235 ml. of formaldehyde diisopropylacetal and 500 ml. of methylene chloride and cooled to −20° C. Under agitation, a mixture of 75 g. of phosphorus pentoxide and 150 g. of kieselguhr is introduced and the mixture is agitated for 20 hours at −20° C. The mixture is filtered, washed with methylene chloride, and brought to pH 9 with triethylamine. The solvents are distilled off under vacuum and the residue taken up in methylene chloride. The solution is washed with semisaturated sodium chloride solution, dried with sodium sulfate, treated with activated carbon, vacuum-filtered over kieselguhr, and concentrated under vacuum. The residue is chromatographed on silica gel with toluene/ethyl acetate mixtures. Yield: 35.8 g. of 21-acetoxy-17α-isopropoxymethoxy-4-pregnene-3,20-dione, m.p. after crystallization with pentane: 111°–117° C.

(b) *Curvularia lunata* NRRL 2380 is incubated—as described in Example 13(b)—in a shaker flask, a preliminary fermentor, and a main fermentor. At the tenth hour in the main fermentor, 12 g. of 21-acetoxy-17α-isopropoxymethoxy-4-pregnene-3,20-dione is added in 240 ml. of ethylene glycol monomethyl ether. The pH is maintained from this point in time at between 6.5 and 7.0, and fermentation is continued for another 15 hours. The fermentation culture is worked up—as described in Example 13(b)—thus obtaining 8.4 g. of 11β,21-dihydroxy-17α-isopropoxymethoxy-4-pregnene-3,20-dione, m.p. 71°/73°–78° C.

(c) *Arthrobacter simplex* ATCC 6946 is grown—as described in Example 11—in an incubation flask and a fermentation flask. At the sixth hour in the fermentation flask, 1 ml. of a sterile solution of 50 mg. of 11β,21-dihydroxy-17α-isopropoxymethoxy-4-pregnene-3,20-dione in ethylene glycol monomethyl ether is added, and the mixture is fermented for another 42 hours.

The fermentation culture is worked up as described in Example 1(b), thus obtaining 32 mg. of 11β,21-dihydroxy-17α-isopropoxymethoxy-1,4-pregnadiene-3,20-dione, m.p. 58°/63°-65° C.

EXAMPLE 56

(a) 10.0 g. of prednisolone 21-acetate is dissolved with 40 g. of 4-dimethylaminopyridine and 500 ml. of methylene chloride, cooled to −15° C., and combined with 25 ml. of acetic anhydride. Within 10 minutes, 10 ml. of formic acid is added dropwise and the mixture agitated for another 135 minutes at −10° to −15° C. The solution is extracted with water, 4% strength hydrochloric acid, and sodium bicarbonate solution; the organic phase is dried with sodium sulfate and concentrated under vacuum. The residue is recrystallized from methanol with the addition of a small amount of methylene chloride, thus producing 9.34 g. of 21-acetoxy-11β-formyloxy-17α-17α-hydroxy-1,4-pregnadiene-3,20-dione, m.p. 221°-223° C.

(b) 5.0 g. of 21-acetoxy-11β-formyloxy-17α-hydroxy-1,4-pregnadiene-3,20-dione is dissolved in 150 ml. of methylene chloride and 30 ml. of formaldehyde diethylacetal and cooled to 0° C. Under agitation, a mixture of 5 g. of phosphorus pentoxide and 10 g. of kieselguhr is inroduced, and the mixture is stirred for 2.5 hours in an ice bath, whereafter it is filtered, washed with methylene chloride, and brought to pH 9 with triethylamine. After the solvent has been distilled off, 10.5 g. of crude 21-acetoxy-17α-ethoxymethoxy-11β-formyloxy-1,4-pregnadiene-3,20-dione is obtained as a semisolid mass.

(c) 0.34 g. of crude 21-acetoxy-17α-ethoxymethoxy-11β-formyloxy-1,4-pregnadiene-3,20-dione is dissolved in 13 ml. of methanol and added under argon to a solution of 0.126 g. of sodium bicarbonate in 1.32 ml. of water at a temperature of 60° C. The mixture is heated under reflux for 10 minutes, cooled off, combined with water, and extracted with methylene chloride. The methylene chloride solution is dried with sodium sulfate, concentrated, and the residue chromatographed over silica gel with toluene/ethyl acetate mixtures, thus obtaining 0.1 g. of 17α-ethoxymethoxy-11β,21-dihydroxy-1,4-pregnadiene-3,20-dione, m.p. 149.5°-152° C.

EXAMPLE 57

(a) 20.0 g. of 11β,21-dihydroxy-17α-methoxymethoxy-4-pregnene-3,20-dione is dissolved in 200 ml. of pyridine and, under cooling, 20 ml. of methanesulfonic acid chloride is added dropwise thereto. The mixture is stirred for 30 minutes at room temperature and precipitated into 2000 ml. of ice water. After vacuum-filtering, washing, and drying, 23.85 g. of 11β-hydroxy-21-methanesulfonyloxy-17α-methoxymethoxy-4-pregnene-3,20-dione is obtained, decomposition point 154°-155° C.

(b) 20 g. of 11β-hydroxy-21-methanesulfonyloxy-17α-methoxymethoxy-4-pregnene-3,20-dione is combined with 600 ml. of acetone; a solution of 20 g. of sodium iodide in 520 ml. of acetone is added thereto, and the mixture is heated under reflux for 11 hours. After cooling, the mixture is filtered off from insoluble matter, the acetone solution is concentrated under vacuum, and the residue is combined with water and a small amount of sodium thiosulfate solution. The crude product is vacuum-filtered, washed with water, and recrystallized from acetone, thus obtaining 16.6 g. of 11β-hydroxy-21-iodo-17α-methoxymethoxy-4-pregnene-3,20-dione, decomposition point 123°-126° C.

(c) One gram of 11β-hydroxy-21-iodo-17α-methoxymethoxy-4-pregnene-3,20-dione is heated with 20 ml. of toluene and 1.3 ml. of tributyltin hydride under argon for 30 minutes to 55° C. The toluene is then distilled off under vacuum, and the residue is treated with pentane. The crystallized product is 0.64 g. of 11β-hydroxy-17α-methoxymethoxy-4-pregnene-3,20-dione, m.p. 191°-194° C.

EXAMPLE 58

(a) 9.0 g. of 21-acetoxy-17α-hydroxy-4,9(11)-pregnadiene-3,20-dione is dissolved together with 72 ml. of formaldehyde diethylacetal and 280 ml. of methylene chloride and cooled to 0° C. Under agitation, a mixture of 9.0 g. of phosphorus pentoxide and 18 g. of kieselguhr is introduced and the mixture stirred for 2.5 hours in an ice bath. The mixture is filtered and washed with methylene chloride. The solution is brought to pH 9 with triethylamine, concentrated, and the residue chromatographed on silica gel with toluene/ethyl acetate mixtures. Yield: 5.93 g. of 21-acetoxy-17α-ethoxymethoxy-4,9(11)-pregnadiene-3,20-dione, m.p. 167°-169° C.

(b) 5.8 g. of 21-acetoxy-17α-ethoxymethoxy-4,9(11)-pregnadiene-3,20-dione is reacted under the conditions set forth in Example 26(b), but without recrystallization, thus obtaining 7.6 g. of crude 21-acetoxy-17α-ethoxymethoxy-9α-bromo-11β-hydroxy-4-pregnene-3,20-dione as a vitreous substance.

(c) 7.6 g. of crude 21-acetoxy-17α-ethoxymethoxy-9α-bromo-11β-hydroxy-4-pregnene-3,20-dione is reacted under the conditions mentioned in Example 26(c), and the methanolic solution of the crude product is filtered over silica gel, thus obtaining 5.49 g. of crude 21-acetoxy-17α-ethoxymethoxy-9β,11β-epoxy-4-pregnene-3,20-dione as an amorphous substance.

(d) 5.4 g. of crude 21-acetoxy-17α-ethoxymethoxy-9β,11β-epoxy-4-pregnene-3,20-dione is reacted under the conditions set forth in Example 26(d). The crude product is chromatographed on silica gel with toluene/ethyl acetate mixtures, thus obtaining 1.78 g. of 21-acetoxy-17α-ethoxymethoxy-9α-chloro-11β-hydroxy-4-pregnene-3,20-dione, m.p. 148°-151° C.

EXAMPLE 59

(a) 6.0 g. of hydrocortisone 21-acetate-11-formate is dissolved in 150 ml of methylene chloride and 63 g. of formaldehyde dihexylacetal and cooled to 10° C. Under argon, a mixture of 6 g. of phosphorus pentoxide and 12 g. of kieselguhr is added in incremental portions, and the mixture is agitated for one hour at 10° C. and for one hour at 15° C. The mixture is filtered, washed with methylene chloride, and brought to pH 8 with triethylamine. The methylene chloride is evaporated under vacuum, and the residue is cooled in an ice bath. The solution is decanted off from the thus-precipitated oil and chromatographed on silica gel with toluene/ethyl acetate mixtures, thus obtaining 4.2 g. of 21-acetoxy-11β-formyloxy-17α-hexyloxymethoxy -4-pregnene-3,20-dione, m.p. 110° C. after crystallization with pentane.

(b) 0.38 g. of 21-acetoxy-11β-formyloxy-17α-hexyloxymethoxy-4-pregnene-3,20-dione is reacted under the conditions described in Example 56(c), thus obtaining 0.1 g. of 11β,21-dihydroxy-17α-hexyloxymethoxy-4-pregnene-3,20-dione.

EXAMPLE 60

(a) 6.0 g. of hydrocortisone 21-acetate-11-formate is dissolved in 150 ml. of methylene chloride and 65 g. of formaldehyde dibenzyacetal and then, under argon in a water bath at room temperature, a mixture of 6 g. of phosphorus pentoxide and 12 g. of kieselguhr is added in incremental portions under stirring. After four hours, the mixture is filtered, washed with methylene chloride, and brought to pH 8 with triethylamine. The methylene chloride is evaporated under vacuum and the residue chromatographed on silica gel with toluene/ethyl acetate mixtures, yielding 3.0 g. of 21-acetoxy-17α-benzyloxymethoxy-11β-formyloxy-4-pregnene-3,20-dione.

(b) 0.38 g. of 21-acetoxy-17α-benzyloxymethoxy-11β-formyloxy-4-pregnene-3,20-dione is reacted under the conditions described in Example 56(c), thus obtaining 0.11 g. of 17α-benzyloxymethoxy-11β,21-dihydroxy-4-pregnene-3,20-dione.

EXAMPLE 61

(a) *Flavobacterium dehydrogenans* ATCC 13930 is grown—as described in Example 1.—in a shaker flask, a preliminary fermentor, and a main fermentor. At the 24th hour in the main fermentor, 19.5 g. of 16-methylene-3β,21-diacetoxy-17α-methoxymethoxy-5-pregnen-20-one in 500 ml. of dimethylformamide is added to the content and the latter fermented for another 28 hours. The fermentation culture is worked up—as described in Example 13(b)—thus obtaining 15.5 g. of 16-methylene-21-hydroxy-17α-methoxymethoxy-4-pregnene-3,20-dione, m.p. 147°/150°-151° C.

(b) *Curvularia lunata* NRRL 2380 is germinated—as described in Example 13(b)—in a shaker flask, a preliminary fermentor, and a main fermentor. At the tenth hour in the main fermentor, 20 g. of 16-methylene-21-hydroxy-17α-methoxymethoxy-4-pregnene-3,20-dione is added in 400 ml. of ethylene glycol monomethyl ether. The pH is maintained, from this point in time on, between 6.4 and 6.7, and the fermentation is continued for another 8 hours.

The fermentation culture is worked up—as described in Example 13(b)—yielding 11 g. of 16-methylene-11β,21-dihydroxy-17α-methoxymethoxy-4-pregnene-3,20-dione, m.p. 205°/206°-208° C.

EXAMPLE 62

*Arthrobacter simplex* ATCC 6946 is grown—as described in Example 11—in a germination flask and a fermentation flask. At the sixth hour in the fermentation flask, 1 ml. of a sterile solution of 50 mg. of 11β,21-dihydroxy-17α-propoxymethoxy-4-pregnene-3,20-dione is added in ethylene glycol monomethyl ether, and the content is fermented for another 42 hours. The fermentation culture is worked up—as described in Example 1(b)—yielding 41 mg. of 11β,21-dihydroxy-17α-propoxymethoxy-1,4-pregnadiene-3,20-dione, m.p 121°/125°-127° C.

EXAMPLE 63

3.0 g. of 11β,21-dihydroxy-17α-methoxymethoxy-16-methylene-4-pregnene-3,20-dione is dissolved in 12 ml. of pyridine at +20° C. and combined with 2.37 ml. of acetic anhydride. The reaction mixture is stirred for 2 hours at +20° C. and then precipitated into 144 ml. of ice water. The mixture is stirred for one hour; the crystallized product is vacuum-filtered, washed with water, and dried. Recrystallization from ethyl acetate yields 2.74 g. of 21-acetoxy-11β-hydroxy-17α-methoxymethoxy-16-methylene-4-pregnene-3,20-dione, m.p. 166°-167° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A corticoid of the formula

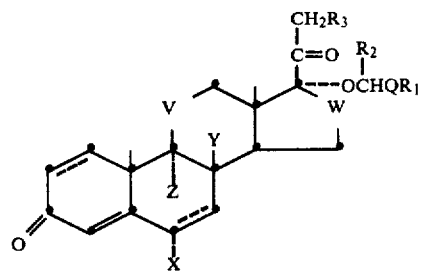

wherein

= represents a single bond or a double bond;

X is hydrogen, fluorine, chlorine or methyl;

Y is hydrogen and Z is hydrogen, fluorine or chlorine, or

Y and Z together are a carbon-to-carbon bond;

V is β-hydroxymethylene, β-chloromethylene or carbonyl;

W is methylene, ethylidene or vinylidene;

Q is oxygen or sulfur;

$R_1$ is alkyl of 1-8 carbon atoms, alkyl of 2-8 carbon atoms with an oxygen atom between two of the carbon atoms or benzyl, and $R_2$ is hydrogen or alkyl of 1-4 carbon atoms, or $R_1$ and $R_2$ collectively are trimethylene or tetramethylene; and $R_3$ is hydrogen, fluorine, chlorine, hydroxy or hydroxy esterified by a $C_{1-16}$ hydrocarbon carboxylic acid.

2. A corticoid of claim 1 of the formula

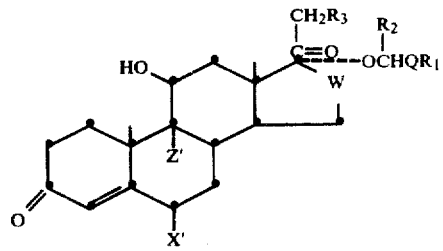

wherein

X' is hydrogen, fluorine, or methyl and

Z' is hydrogen, fluorine or chlorine.

3. A corticoid of claim 1 of the formula

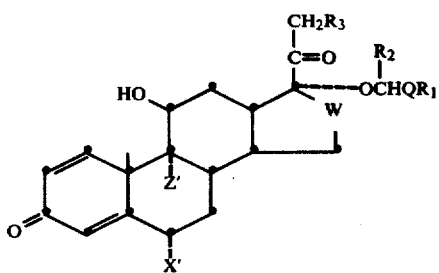

wherein

X' is hydrogen, fluorine or methyl and
Z' is hydrogen, fluorine or chlorine.

4. A corticoid of claim 1 of the formula

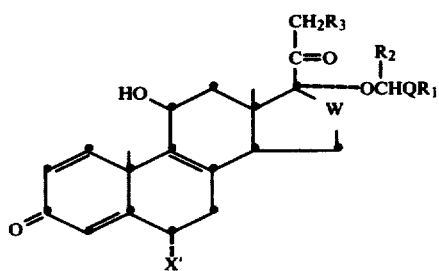

wherein X' is hydrogen, fluorine or methyl.

5. A corticoid of claim 2 or 3, wherein X' is hydrogen.

6. A corticoid of claim 2, 3 or 5, wherein Z' is hydrogen.

7. A corticoid of claim 2, 3 or 5, wherein Z' is fluorine or chlorine.

8. A corticoid of claim 4, wherein X' is hydrogen.

9. A corticoid of claim 1, wherein W is methylene.

10. A corticoid of claim 1, wherein Q is oxygen.

11. A corticoid of claim 1, wherein Q is sulfur.

12. A corticoid of claim 1, wherein $R_2$ is hydrogen.

13. A corticoid of claim 1, wherein $R_2$ is alkyl of 1–16 carbon atoms.

14. A corticoid of claim 1, wherein $R_3$ is hydroxy or hydroxy esterified by a $C_{1-8}$ hydrocarbon carboxylic acid.

15. A corticoid of claim 1, wherein $R_3$ is fluorine or chlorine.

16. 11β,21-Dihydroxy-17α-methoxymethoxy-4-pregnene-3,20-dione, a compound of claim 1.

17. 11β,21-Dihydroxy-17α-(1'-methoxyethoxy)-4-pregnene-3,20-dione, a compound of claim 1.

18. 17α-(1'-Ethoxyethoxy)-11β,21-dihydroxy-4-pregnene-3,20-dione, a compound of claim 1.

19. 11β,21-Dihydroxy-17α-(1'-isobutoxyethoxy)-4-pregnene-3,20-dione, a compound of claim 1.

20. 11β,21-Dihydroxy-17α-(2'-tetrahydropyranyloxy)-4-pregnene-3,20-dione, a compound of claim 1.

21. 11β,21-Dihydroxy-17α-(1'-methoxyethoxy)-6α-methyl-4-pregnene-3,20-dione, a compound of claim 1.

22. 11β,21-Dihydroxy-17α-(1'-methoxyethoxy)-16β-methyl-4-pregnene-3,20-dione, a compound of claim 1.

23. 11β-Hydroxy-17α-(1'-methoxyethoxy)-4-pregnene-3,20-dione, a compound of claim 1.

24. 11β,21-Dihydroxy-17α-(2'-methoxyethoxymethoxy)-4-pregnene-3,20-dione, a compound of claim 1.

25. 11β,21-Dihydroxy-17α-methoxymethoxy-1,4-pregnadiene-3,20-dione, a compound of claim 1.

26. 11β,21-Dihydroxy-17α-(1'-methoxyethoxy)-6α-methyl-1,4-pregnadiene-3,20-dione, a compound of claim 1.

27. 11β,21-Dihydroxy-17α-ethoxymethoxy-4-pregnene-3,20-dione, a compound of claim 1.

28. 11β,21-Dihydroxy-17α-propoxymethoxy-4-pregnene-3,20-dione, a compund of claim 1.

29. 11β,21-Dihydroxy-17α-butoxymethoxy-4-pregnene-3,20-dione, a compound of claim 1.

30. 11β,21-Dihydroxy-6α-fluoro-17α-methoxymethoxy-4-pregnene-3,20-dione, a compound of claim 1.

31. 11β,21-Dihydroxy-17α-methoxymethoxy-16β-methyl-4-pregnene-3,20-dione, a compound of claim 1.

32. 21-Acetoxy-11β-hydroxy-17α-methoxymethoxy-4-pregnene-3,20-dione, a compound of claim 1.

33. 11β-Hydroxy-17α-methoxymethoxy-21-propionyloxy-4-pregnene-3,20-dione, a compound of claim 1.

34. 21-Butyryloxy-11β-hydroxy-17α-methoxymethoxy-4-pregnene-3,20-dione, a compound of claim 1.

35. 11β-Hydroxy-17α-methoxymethoxy-21-trimethylacetoxy-4-pregnene-3,20-dione, a compound of claim 1.

36. 21-Acetoxy-11β-hydroxy-17α-methoxymethoxy-1,4-pregnadiene-3,20-dione, a compound of claim 1.

37. 21-Butyryloxy-11β,17α-methoxymethoxy-1,4-pregnadiene-3,20-dione, a compound of claim 1.

38. 21-Acetoxy-17α-methoxymethoxy-4-pregnene-3,11,20-trione, a compound of claim 1.

39. 21-Acetoxy-9α-chloro-11β-hydroxy-17α-methoxymethoxy-4-pregnene-3,20-dione, a compound of claim 1.

40. 21-Acetoxy-9α-fluoro-11β-hydroxy-17α-methoxymethoxy-4-pregnene-3,20-dione, a compund of claim 1.

41. 9α-Chloro-11β,21-dihydroxy-17α-methoxymethoxy-4-pregnene-3,20-dione, a compound of claim 1.

42. 21-Acetoxy-11β-hydroxy-17α-methylthiomethoxy-1,4-pregnadiene-3,20-dione, a compound of claim 1.

43. 21-Acetoxy-9α-fluoro-11β-hydroxy-17α-methylthiomethoxy-4-pregnene-3,20-dione, a compound of claim 1.

44. 21-Acetoxy-9α-chloro-17α-(2'-methoxyethoxymethoxy)-1,4-pregnadiene-3,20-dione, a compound of claim 1.

45. 21-Acetoxy-9α,11β-dichloro-17α-(2'-methoxyethoxymethoxy)-1,4-pregnadiene-3,20-dione, a compound of claim 1.

46. 21-Acetoxy-9α-chloro-11β-hydroxy-17α-methoxymethoxy-1,4-pregnadiene-3,20-dione, a compound of claim 1.

47. 21-Acetoxy-9α,11β-dichloro-17α-methoxymethoxy-1,4-pregnadiene-3,20-dione, a compound of claim 1.

48. 21-Acetoxy-11β-hydroxy-17α-(2'-methoxyethoxymethoxy)-1,4,8-pregnatriene-3,20-dione, a compound of claim 1.

49. 9α,21-Dichloro-11β-hydroxy-17α-methoxymethoxy-4-pregnene-3,20-dione, a compound of claim 1.

50. 9α-Chloro-21-fluoro-11β-hydroxy-17α-methoxymethoxy-1,4-pregnadiene-3,20-dione, a compound of claim 1.

51. 9α-Chloro-11β-hydroxy-17α-methoxymethoxy-1,4-pregnadiene-3,20-dione, a compound of claim 1.

52. 21-Fluoro-11β-hydroxy-17α-methoxymethoxy-1,4,8-pregnatriene-3,20-dione, a compound of claim 1.

53. 21-Chloro-11β-hydroxy-17α-methoxymethoxy-1,4,8-pregnatriene-3,20-dione, a compound of claim 1.

54. 9α-Chloro-21-fluoro-11β-hydroxy-17α-methoxymethoxy-4-pregnene-3,20-dione, a compound of claim 1.

55. 9α-Fluoro-11β-hydroxy-17α-methoxymethoxy-21-propionyloxy-1,4-pregnadiene-3,20-dione, a compound of claim 1.

56. 21-Butyryloxy-9α-fluoro-11β-hydroxy-17α-methoxymethoxy-1,4-pregnadiene-3,20-dione, a compound of claim 1.

57. 21-Butyryloxy-9α-fluoro-17α-methoxymethoxy-1,4-pregnadiene-3,11,20-trione, a compound of claim 1.

58. 21-Butyryloxy-9α-fluoro-17α-(2'-methoxyethoxymethoxy)-1,4-pregnadiene-3,11,20-trione, a compound of claim 1.

59. 9α-Fluoro-11β-hydroxy-17α-methoxymethoxy-16β-methyl-21-propionyloxy-1,4-pregnadiene-3,20-dione, a compound of claim 1.

60. 9α-Fluoro-11β-hydroxy-17α-methoxymethoxy-16β-methyl-21-propionyloxy-4-pregnene-3,20-dione, a compound of claim 1.

61. 9α-Fluoro-11β,21-dihydroxy-17α-methoxymethoxy-16β-methyl-1,4-pregnadiene-3,20-dione, a compound of claim 1.

62. 21-Chloro-9α-fluoro-11β-hydroxy-17α-methoxymethoxy-16β-methyl-1,4-pregnadiene-3,20-dione, a compound of claim 1.

63. 21-Butyryloxy-9α-fluoro-11β-hydroxy-17α-methoxymethoxy-4-pregnene-3,20-dione, a compound of claim 1.

64. 9α-Fluoro-11β-hydroxy-17α-methoxymethoxy-21-valeryloxy-4-pregnene-3,20-dione, a compound of claim 1.

65. 21-chloro-9α-fluoro-11β-hydroxy-17α-methoxymethoxy-1,4-pregnadiene-3,20-dione, a compound of claim 1.

66. 11β,21-Dihydroxy-6-chloro-17α-methoxymethoxy-4,6-pregnadiene-3,20-dione, a compound of claim 1.

67. 11β,21-Dihydroxy-17α-isopropoxymethoxy-4-pregnene-3,20-dione, a compound of claim 1.

68. 11β,21-Dihydroxy-17α-isopropoxymethoxy-1,4-pregnadiene-3,20-dione, a compound of claim 1.

69. 17α-Ethoxymethoxy-11β,21-dihydroxy-1,4-pregnadiene-3,20-dione, a compound of claim 1.

70. 11β-Hydroxy-17α-methoxymethoxy-4-pregnene-3,20-dione, a compound of claim 1.

71. 21-Acetoxy-17α-ethoxymethoxy-9α-chloro-11β-hydroxy-4-pregnene-3,20-dione, a compound of claim 1.

72. 11β,21-Dihydroxy-17α-hexyloxymethoxy-4-pregnene-3,20-dione, a compound of claim 1.

73. 17α-Benzyloxymethoxy-11β,21-dihydroxy-4-pregenen-3,20-dione, a compound of claim 1.

74. 11β,21-Dihydroxy-17α-methoxymethoxy-16-methylene-4-pregnene-3,20-dione, a compound of claim 1.

75. 11β,21-Dihydroxy-17α-propoxymethoxy-1,4-pregnadiene-3,20-dione, a compound of claim 1.

76. 21-Acetoxy-11β-hydroxy-17α-methoxymethoxy-16-methylene-4-pregnene-3,20-dione, a compound of claim 1.

77. A pharmaceutical composition comprising an anti-inflammatorily effective amount of a compound of claim 1 and a pharmaceutically acceptable carrier.

78. A method of treating inflammation in mammals which comprises administering an anti-inflammatorily effective amount of a compound of claim 1.

79. A process for preparing a steroid of the formula

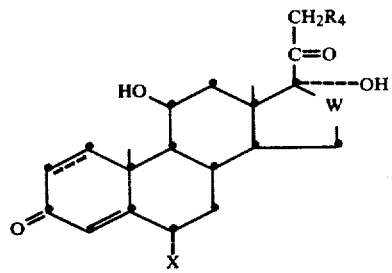

wherein
= and W are as defined in 1, R₄ is H or OH, which comprises deacetalizing a compound of the formula

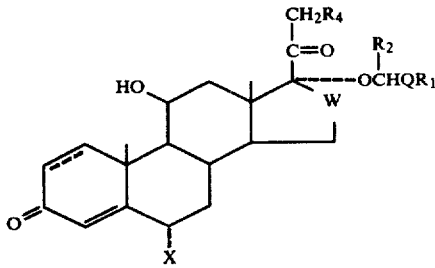

wherein Q, R₁ and R₂ are also as defined in claim 1, by treating it under acidic conditions effective to cleave the acetal group.

* * * * *